United States Patent [19]

Fujimoto et al.

[11] Patent Number: 4,977,144
[45] Date of Patent: Dec. 11, 1990

[54] IMIDAZO[4,5-B]PYRIDINE DERIVATIVES AS CARDIOVASCULAR AGENTS

[75] Inventors: Roger A. Fujimoto, West Orange; John E. Francis, Basking Ridge, both of N.J.; Alan J. Hutchison, Madison, Conn.

[73] Assignee: Ciba-Geigy Corporation, Ardsley, N.Y.

[21] Appl. No.: 405,926

[22] Filed: Sep. 12, 1989

Related U.S. Application Data

[63] Continuation-in-part of Ser. No. 229,684, Aug. 2, 1988, abandoned.

[51] Int. Cl.$^5$ .................. A61K 31/70; A61K 31/44; C07H 17/00; C07D 401/00
[52] U.S. Cl. .................................. 514/46; 536/24; 514/293; 514/303; 546/256; 546/271; 546/118
[58] Field of Search .................. 546/256, 271, 118; 514/293, 303, 46; 536/24

[56] References Cited

U.S. PATENT DOCUMENTS

| | | | |
|---|---|---|---|
| 4,122,172 | 10/1978 | Langenscheid | 546/256 |
| 4,276,293 | 6/1981 | Lesher et al. | 546/256 |
| 4,714,764 | 12/1987 | Sato et al. | 546/271 |
| 4,780,452 | 10/1988 | Krenitsky et al. | 546/256 |

FOREIGN PATENT DOCUMENTS

| | | | |
|---|---|---|---|
| 38161 | 10/1981 | European Pat. Off. | 546/256 |
| 155094 | 9/1985 | European Pat. Off. | 546/256 |
| 260852 | 3/1988 | European Pat. Off. | 546/256 |
| 269574 | 6/1988 | European Pat. Off. | 546/256 |
| 277917 | 8/1988 | European Pat. Off. | 546/256 |
| 323807 | 7/1989 | European Pat. Off. | 546/256 |

OTHER PUBLICATIONS

Nucleosides and Nucleotides, 4, 625–639 (1985).
J. Pharmaceutical Sciences 73, 366 (1984).
J. Med. Chem. 31, 1179–1183 (1988).
J. Med. Chem. 30, 1686–1688 (1987).
Ital. J. Biochem. 31, 396 (1982).
J. Heterocyclic Chem. 15, 839 (1978).
Chem. Abstracts 105, 38047v (1986).
J. Enzyme Inhibition I, 67–75 (1985).

Primary Examiner—Mary C. Lee
Assistant Examiner—Robert C. Whittenbaugh
Attorney, Agent, or Firm—Norbert Gruenfeld

[57] ABSTRACT

Disclosed are the compounds of the formula

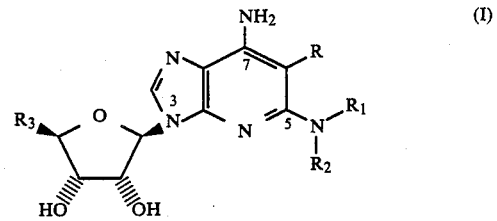

wherein R represents hydrogen, lower alkyl, aryl or aryl-lower alkyl; $R_1$ represents hydrogen, lower alkyl, $C_3$–$C_7$-alkenyl, carbocyclic or heterocyclic aryl, carbocyclic or heterocyclic aryl-lower alkyl, $C_3$–$C_7$-cycloalkyl, or optionally lower alkyl substituted ($C_3$–$C_7$-cycloalkyl, bicycloheptyl, bicycloheptenyl, adamantyl, tetrahydropyranyl or tetrahydrothiopyranyl)-lower alkyl, or diaryl-lower alkyl; $R_2$ represents hydrogen or lower alkyl; $R_3$ represents hydroxymethyl or —$CONHR_4$ in which $R_4$ represents hydrogen, lower alkyl, aryl-lower alkyl, $C_3$–$C_7$-cycloalkyl, $C_3$–$C_7$-cycloalkyl-lower alkyl or hydroxy-lower alkyl; pharmaceutically acceptable ester derivatives thereof in which one or more of the hydroxy groups are esterified in form of a pharmaceutically acceptable ester; and pharmaceutically acceptable salts thereof; methods of preparation; pharmaceutical compositions; and their use as adenosine-2 agonists in mammals.

24 Claims, No Drawings

IMIDAZO[4,5-B]PYRIDINE DERIVATIVES AS CARDIOVASCULAR AGENTS

CROSS-REFERENCE TO RELATED APPLICATIONS

This application is a continuation-in-part of application Ser. No. 229,684 filed Aug. 2, 1988, now abandoned.

SUMMARY OF THE INVENTION

The instant invention is directed to certain imidazo-[4,5-b]pyridine derivatives as adenosine receptor ligands, to pharmaceutical compositions thereof, to methods for their preparation, and to their use in mammals as therapeutically effective adenosine agonists.

The compounds of the invention are particularly effective as adenosine-2 (A-2) receptor ligands which are useful in mammals as adenosine-2 (A-2) agonists.

Said advantageous properties render the compounds of the invention useful for the treatment of conditions in mammals responsive to adenosine-2 agonist activity e.g. cardiovascular conditions such as hypertension, thrombosis and atherosclerosis.

DETAILED DESCRIPTION OF THE INVENTION

The instant invention is directed to the imidazo-[4,5-b]pyridine derivatives of the formula I

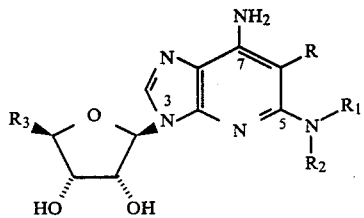

wherein R represents hydrogen, lower alkyl, carbocyclic aryl or carbocyclic aryl-lower alkyl; $R_1$ represents hydrogen, lower alkyl, $C_3$–$C_7$-alkenyl, carbocyclic or heterocyclic aryl, carbocyclic or heterocyclic aryl-lower alkyl, $C_3$–$C_7$-cycloalkyl, or optionally lower alkyl-substituted ($C_3$–$C_7$-cycloalkyl, bicycloheptyl, bicycloheptenyl, adamantyl, tetrahydropyranyl or tetrahydrothiopyranyl)-lower alkyl, or diaryl-lower alkyl; $R_2$ represents hydrogen or lower alkyl; $R_3$ represents hydroxymethyl or —$CONHR_4$ in which $R_4$ represents hydrogen, lower alkyl, aryl-lower alkyl, $C_3$–$C_7$-cycloalkyl, $C_3$–$C_7$-cycloalkyl-lower alkyl or hydroxy-lower alkyl; pharmaceutically acceptable ester derivatives thereof in which one or more of the hydroxy groups are esterified in form of a pharmaceutically acceptable ester; and pharmaceutically acceptable salts thereof.

Preferred are the compounds of formula I wherein R represents hydrogen or lower alkyl; $R_1$ represents hydrogen, lower alkyl, $C_3$–$C_7$-cycloalkyl-lower alkyl, adamantyl-lower alkyl, bicycloheptyl-lower alkyl, aryl or aryl-lower alkyl in which aryl represents phenyl, thienyl, pyridyl, naphthyl, or phenyl substituted by one to three substituents selected from halogen, trifluoromethyl, lower alkoxy and lower alkyl, or aryl represents phenyl substituted by a substituent —W—Z in which W represents a direct bond, lower alkylene or oxy-lower alkylene, and Z represents hydroxy, cyano, carboxy, carboxy derivatized in the form of a pharmaceutically acceptable ester, carboxy derivatized in the form of a pharmaceutically acceptable amide, phenyl or phenyl substituted by halogen, trifluoromethyl, lower alkyl or lower alkoxy; or $R_1$ represents diaryl-lower alkyl in which aryl represents phenyl or phenyl substituted by halogen, trifluoromethyl, lower alkoxy or lower alkyl; $R_2$ represents hydrogen or lower alkyl; $R_3$ represents hydroxymethyl or —$CONHR_4$ in which $R_4$ represents lower alkyl, hydroxy-lower alkyl, $C_3$–$C_6$-cycloalkyl, $C_3$–$C_6$-cycloalkyl-lower alkyl or aryl-lower alkyl in which aryl represents thienyl, naphthyl, phenyl, or phenyl substituted by halogen, trifluoromethyl, lower alkoxy, lower alkyl, hydroxy, cyano, carboxy, carboxy derivatized in the form of a pharmaceutically acceptable ester or carboxy derivatized in the form of a pharmaceutically acceptable amide; pharmaceutically acceptable ester derivatives thereof in which one or more hydroxy groups are esterified in the form of a pharmaceutically acceptable ester; and pharmaceutically acceptable salts thereof.

A particular embodiment of the invention relates to the compounds of formula I cited hereinabove wherein $R_3$ represents —$CONHR_4$ as defined, and R, $R_1$ and $R_2$ have meaning as defined above; pharmaceutically acceptable ester derivatives thereof as defined above; and pharmaceutically acceptable salts thereof.

Another particular embodiment relates to the compounds of formula I wherein $R_3$ represents hydroxymethyl, and R, $R_1$ and $R_2$ have meaning as defined above; pharmaceutically acceptable ester derivatives as defined above; and pharmaceutically acceptable salts thereof.

Preferred are the said compounds of the invention wherein R represents hydrogen; also wherein $R_2$ represents hydrogen.

A particular embodiment of the invention relates to the compounds of formula II

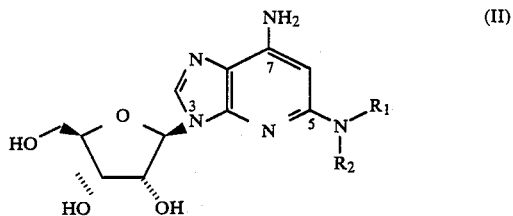

wherein $R_1$ represents bicycloheptyl-lower alkyl, adamantyl-lower alkyl, $C_3$–$C_7$-cycloalkyl-lower alkyl, aryl or aryl-lower alkyl in which aryl represents thienyl, pyridyl, phenyl or phenyl substituted by halogen, trifluoromethyl, lower alkoxy, lower alkyl or a substituent —W—Z in which W represents a direct bond, lower alkylene or oxy-lower alkylene, and Z represents hydroxy, cyano, carboxy, lower alkoxycarbonyl, carbamoyl, N-mono- or N,N-di-lower alkylcarbamoyl, or phenyl; $R_2$ represents hydrogen or $C_1$–$C_3$-alkyl; pharmaceutically acceptable prodrug ester derivatives thereof in which one or more of the hydroxy groups are esterified in form of a pharmaceutically acceptable ester; and pharmaceutically acceptable salts thereof.

Preferred are compounds of formula II wherein $R_1$ represents —$(CH_2)_n$—$R_5$; n represents an integer from 2 to 5 inclusive; $R_5$ represents thienyl, pyridyl, phenyl or phenyl substituted by halogen, trifluoromethyl, lower alkoxy, lower alkyl or by a substituent —W—Z in which W represents a direct bond, $C_1$–$C_4$-alkylene or oxy-$C_1$-$C_3$-alkylene and Z represents hydroxy, cyano, carboxy, lower alkoxycarbonyl, carbamoyl, N-mono- or N,N-di-lower alkyl-carbamoyl, or phenyl; or $R_5$ represents $C_5$-$C_7$-cycloalkyl, norbornanyl or adamantyl; $R_2$ represents hydrogen; pharmaceutically acceptable ester derivatives thereof in which one or more of the hydroxy groups are esterified in form of a pharmaceutically acceptable ester; and pharmaceutically acceptable salts thereof.

Further preferred are said compounds wherein $R_5$ represents cyclohexyl, phenyl or phenyl substituted by $C_1$-$C_4$-alkyl, $C_1$-$C_4$-alkoxy or trifluoromethyl.

A particular preferred embodiment is represented by said compounds of formula II wherein in —$(CH_2)_n$—$R_5$, n represents the integer 2, 3 or 4, advantageously 2; and $R_5$ represents phenyl or phenyl substituted by $C_1$-$C_4$-alkyl, $C_1$-$C_4$-alkoxy, halogen or trifluoromethyl; or $R_5$ represents phenyl substituted by phenethyl.

Another preferred embodiment of the invention relates to compounds of formula II wherein $R_1$ represents thienyl, pyridyl, phenyl or phenyl substituted by halogen, trifluoromethyl, lower alkoxy, lower alkyl, hydroxy, cyano, carboxy, lower alkoxycarbonyl, carbamoyl, N-mono or N,N-di-lower alkylcarbamoyl; $R_2$ represents hydrogen; pharmaceutically acceptable prodrug ester derivatives thereof in which one or more of the hydroxy groups are esterified in form of a pharmaceutically acceptable ester; and pharmaceutically acceptable salts thereof.

Another embodiment of the invention relates to the compounds of formula III

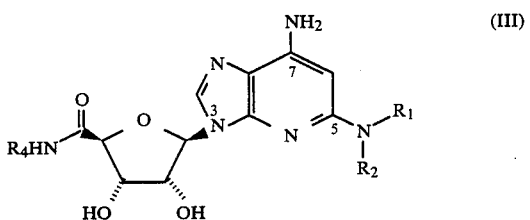

(III)

wherein $R_1$ represents bicycloheptyl-lower alkyl, adamantyl-lower alkyl, $C_3$-$C_7$-cycloalkyl-lower alkyl, aryl or aryl-lower alkyl in which aryl represents thienyl, pyridyl, phenyl or phenyl substituted by halogen, trifluoromethyl, lower alkoxy, lower alkyl or a substituent —W—Z in which W represents a direct bond, lower alkylene or oxy-lower alkylene, and Z represents hydroxy, cyano, carboxy, lower alkoxycarbonyl, carbamoyl, N-mono- or N,N-di-lower alkylcarbamoyl, or phenyl; $R_2$ represents hydrogen; $R_4$ represents $C_1$-$C_4$-alkyl, cyclopropyl or hydroxy-$C_2$-$C_4$-alkyl; pharmaceutically acceptable prodrug ester derivatives thereof in which the hydroxy groups are esterified in form of a pharmaceutically acceptable ester; and pharmaceutically acceptable salts thereof.

Preferred are compounds of formula III wherein $R_1$ represents —$(CH_2)_n$—$R_5$; n represents an integer from 2 to 5 inclusive; $R_5$ represents thienyl, pyridyl, phenyl or phenyl substituted by halogen, trifluoromethyl, lower alkoxy, lower alkyl or by a substituent —W—Z in which W represents a direct bond, $C_1$-$C_4$-alkylene or oxy-$C_1$-$C_3$-alkylene and Z represents hydroxy, cyano, carboxy, lower alkoxycarbonyl, carbamoyl, N-mono- or N,N-di-lower alkylcarbamoyl, or phenyl; or $R_5$ represents $C_5$-$C_7$-cycloalkyl, norbornanyl or adamantyl; $R_2$ represents hydrogen; $R_4$ represents $C_1$-$C_3$-alkyl or cyclopropyl; pharmaceutically acceptable prodrug ester derivatives thereof in which the hydroxy groups are esterified in form of a pharmaceutically acceptable ester; and pharmaceutically acceptable salts thereof.

Further preferred are said compounds wherein $R_5$ represents cyclohexyl, phenyl or phenyl substituted by $C_1$-$C_4$-alkyl, $C_1$-$C_4$-alkoxy or trifluoromethyl.

A particular preferred embodiment is represented by said compounds of formula III wherein in $(CH_2)_nR_5$, n represents the integer 2, 3 or 4, advantageously 2; and $R_5$ represents phenyl or phenyl substituted by $C_1$-$C_4$-alkyl, $C_1$-$C_4$-alkoxy, halogen or trifluoromethyl; or $R_5$ represents phenyl substituted by phenethyl.

Another preferred embodiment of the invention relates to compounds of formula III wherein $R_1$ represents thienyl, pyridyl, phenyl or phenyl substituted by halogen, trifluoromethyl, lower alkoxy, lower alkyl, hydroxy, cyano, carboxy, lower alkoxycarbonyl, carbamoyl, N-mono or N,N-di-lower alkylcarbamoyl; $R_2$ represents hydrogen; $R_4$ represents $C_1$-$C_3$-alkyl or cyclopropyl; pharmaceutically acceptable prodrug ester derivatives thereof in which the hydroxy groups are esterified in form of a pharmaceutically acceptable ester; and pharmaceutically acceptable salts thereof.

The compounds of the invention, of formula I to III and derivatives thereof, are derivatives of β-D-ribofuranose and are thus optically active. In addition, compounds of the invention may contain one or more additional asymmetric carbon atoms, e.g. within the 5-substituent.

Thus, the compounds of the invention can exist in the form of pure enantiomers or diastereoisomers, or mixtures thereof, all of which are within the scope of the invention.

The general definitions used herein have the following meaning within the scope of the present invention.

The term "lower" referred to above and hereinafter in connection with organic radicals or compounds respectively defines such with up to and including 7, preferably up to and including 4 and advantageously one or two carbon atoms.

A lower alkyl group is straight chain or branched and preferably contains 1 to 4 carbon atoms, and represents for example methyl, ethyl, n-propyl or n-butyl.

A lower alkoxy group is straight chain or branched and preferably contains 1 to 4 carbon atoms, and represents for example methoxy, ethoxy, propoxy.

Lower alkylene is straight chain or branched alkylene, preferably straight chain, preferably contains 1 to 4 carbon atoms, and represents for example methylene, ethylene, propylene or butylene.

$C_3$-$C_7$-Alkenyl represents advantageously allyl.

Halogen is preferably chloro, but may also be fluoro, bromo or iodo.

$C_3$-$C_7$-Cycloalkyl represents cyclopropyl, cyclobutyl, cyclopentyl, cyclohexyl or cycloheptyl, preferably cyclopentyl, cyclohexyl, or cyclopropyl, advantageously cyclopropyl as to group $R_4$ in formula III, advantageously cyclohexyl when within group $R_1$.

$C_5$-$C_7$-Cycloalkyl represents cyclopentyl, cyclohexyl or cycloheptyl, preferably cyclohexyl.

Optionally lower alkyl-substituted cycloalkyl-lower alkyl represents preferably (cyclopentyl or cyclohexyl)-$C_1$-$C_4$-alkyl, advantageously (cyclopentyl or cyclohexyl)-ethyl, propyl or butyl optionally substituted by lower alkyl.

Optionally lower alkyl-substituted bicycloheptyl represents preferably unsubstituted or lower alkyl substituted bicyclo[2.2.1]heptyl, such as bornyl, neobornyl, isobornyl, norbornyl, e.g. 2-norbornyl, or unsubstituted or lower alkyl-substituted bicyclo[3.3.1]heptyl, e.g. 6,6-dimethyl-bicyclo[3.1.1]hept-2-yl. The term bornyl is synonymous with bornanyl.

Optionally lower alkyl-substituted bicycloheptenyl represents preferably unsubstituted or lower alkyl-substituted bicyclo[2.2.1]heptenyl, such as norborn-5-en-2-yl, or bicyclo[3.1.1]heptenyl such as 6,6-dimethyl-bicyclo[3.1.1]hept-2-en-2-yl.

Adamantyl represents preferably 1-adamantyl.

Tetrahydropyranyl and tetrahydrothiopyranyl represents preferably 2- or 4-tetrahydropyranyl and 2- or 4-tetrahydrothiopyranyl, respectively.

Aryl represents carbocyclic or heterocyclic aryl.

Carbocyclic aryl represents preferably phenyl, 1- or 2-naphthyl, or phenyl substituted by one to three, advantageously 1 or 2, of lower alkyl, lower alkoxy, halogen or trifluoromethyl. In definitions of $R_1$ and $R_4$, carbocyclic aryl also preferably represents phenyl substituted by a substituent —W—Z, preferably at the para position, in which W represents a direct bond, lower alkylene, or oxy-lower alkylene and Z represents hydroxy, cyano, carboxy or carboxy derivatized in the form of a pharmaceutically acceptable ester or amide; Z may also represent phenyl or phenyl substituted by halogen, trifluoromethyl, lower alkyl or lower alkoxy.

Heterocyclic aryl represents preferably pyridyl, thienyl, pyrrolyl or indolyl, or any said radical substituted by lower alkyl or halogen.

Pyridyl represents 2-, 3- or 4-pyridyl, advantageously 2- or 3-pyridyl.

Thienyl represents 2- or 3-thienyl, advantageously 2-thienyl.

Indolyl represents 2- or 3-indolyl, advantageously 3-indolyl.

Pyrrolyl represents 1,2 or 3-pyrrolyl, advantageously 1-pyrrolyl.

Aryl-lower alkyl represents straight chain or branched aryl-$C_1$-$C_7$-alkyl, preferably straight chain or branched aryl-$C_1$-$C_4$-alkyl, in which aryl has meaning as defined above, e.g. benzyl or 1- or 2-phenyl-(ethyl, propyl or butyl), each unsubstituted or substituted on phenyl ring as defined under carbocyclic aryl above; or 2-, 3- or 4-pyridylmethyl or (2-, 3- or 4-pyridyl)-(ethyl, propyl or butyl); or 1- or 2-naphthylmethyl or (1- or 2-naphthyl)-(ethyl, propyl or butyl); or 2- or 3-thienylmethyl or (2- or 3-thienyl)-(ethyl, propyl or butyl).

Diaryl-lower alkyl represents preferably diphenyl-$C_1$-$C_4$-alkyl, e.g. omega-diphenyl-(methyl, ethyl or propyl).

Hydroxy-lower alkyl represents preferably 2-, 3- or 4-hydroxy-$C_2$-$C_4$-alkyl, advantageously hydroxyethyl.

Carboxy esterified in the form of a pharmaceutically acceptable ester represents advantageously an ester that may be convertible by solvolysis or under physiological conditions to the free carboxylic acid, e.g. lower alkoxycarbonyl; (amino, mono- or di-lower alkylamino)-substituted lower alkoxycarbonyl; carboxy substituted lower alkoxycarbonyl, e.g. alpha-carboxy-substituted lower alkoxycarbonyl; lower alkoxycarbonyl-substituted lower alkoxycarbonyl, e.g. alpha-lower alkoxycarbonyl-substituted lower alkoxycarbonyl; aryl-substituted lower alkoxycarbonyl, e.g. optionally substituted benzyloxycarbonyl or pyridylmethoxycarbonyl; (hydroxy, lower alkanoyloxy or lower alkoxy)-substituted lower alkoxycarbonyl, e.g. pivaloyloxymethoxycarbonyl; (hydroxy, lower alkanoyloxy or lower alkoxy)-substituted lower alkoxymethoxycarbonyl; bicycloalkoxycarbonyl-substituted lower alkoxycarbonyl, e.g. bicyclo[2,2,1]-heptyloxycarbonyl-substituted lower alkoxycarbonyl, especially bicyclo[2,2,1]heptyloxycarbonyl-substituted methoxycarbonyl such as bornyloxycarbonylmethoxycarbonyl; 3-phthalidoxycarbonyl; (lower alkyl, lower alkoxy, halo)-substituted 3-phthalidoxycarbonyl; lower alkoxycarbonyloxy-lower alkoxycarbonyl, e.g. 1-(methoxy- or ethoxycarbonyloxy)-ethoxycarbonyl; aryloxycarbonyl, e.g. phenoxycarbonyl or phenoxycarbonyl advantageously substituted at the ortho position by carboxy or lower alkoxycarbonyl. Preferred are the $C_1$-$C_4$-alkyl esters, omega-(di-lower alkylamino)-alkyl esters, e.g. the di-($C_1$-$C_4$-alkylamino)-ethyl esters, and pivaloyloxymethyl esters.

Carboxy derivatized in the form of a pharmaceutically acceptable amide represents preferably carbamoyl, N-mono-lower alkylcarbamoyl or N,N-di-lower alkylcarbamoyl.

N-Mono- and N,N-di-lower alkylcarbamoyl represent for example N-methyl-, N-ethyl-, N,N-dimethyl- and N,N-diethylcarbamoyl.

The pharmaceutically acceptable ester derivatives in which one or more free hydroxy groups are esterified in the form of a pharmaceutically acceptable ester are particularly prodrug esters that may be convertible by solvolysis under physiological conditions to the compounds of formula I having free hydroxy groups.

Preferred as said prodrug pharmaceutically acceptable esters are straight chain or branched lower alkanoic acid esters, e.g., the acetic, isobutyric, pivaloic acid esters; lower alkoxy-lower alkanoic acid esters, e.g., the methoxyacetic, 3-ethoxypropionic acid esters; arylcarboxylic acid esters, e.g. the benzoic, nicotinic acid esters; carbamic and mono or di-lower alkylcarbamic acid esters (carbamates), e.g. the mono- or di-ethylcarbamic or N-mono- or di-methylcarbamic acid esters. Most preferred are the lower alkanoic acid and lower alkoxyalkanoic acid esters.

A lower alkanoic acid represents preferably a straight chain or branched $C_1$-$C_4$-alkanoic acid, e.g. acetic, isobutyric, pivalic acid.

A lower alkoxy-lower alkanoic acid represents preferably a lower alkoxy-$C_2$-$C_4$-alkanoic acid, e.g. methoxyacetic, 3-ethoxypropionic acid.

An arylcarboxylic acid represents preferably benzoic acid, benzoic acid substituted by one to three of lower alkyl, lower alkoxy, halogen or trifluoromethyl; 2-, 3- or 4-pyridylcarboxylic acid, or 2- or 3-thienylcarboxylic acid.

Pharmaceutically acceptable salts are generally acid addition salts, which are preferably such of therapeutically acceptable inorganic or organic acids, such as strong mineral acids, for example hydrohalic, e.g. hydrochloric or hydrobromic acid; sulfuric, phosphoric or nitric acid; aliphatic or aromatic carboxylic or sulfonic acids, e.g. formic, acetic, propionic, succinic, glycollic, lactic, malic, tartaric, gluconic, citric, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, benzenesulfonic, p-toluenesulfonic, naphthalenesulfonic, sulfanilic, cyclohexylsulfamic acid; or ascorbic acid. For compounds having a free carboxy group, pharmaceutically acceptable salts are also derived from bases, e.g. alkali metal salts, such as the sodium salt, or salts derived from pharmaceutically acceptable amines, such as tromethamine.

The novel compounds of the invention are active in state of the art in vitro and in vivo test systems, indicative of adenosine receptor agonist activity in mammals.

The adenosine receptor agonists of the invention are useful in mammals including man for the treatment of cardiovascular disorders, particularly hypertension and thrombosis.

The above-cited properties are demonstrable in vitro and in vivo tests, using advantageously mammals, e.g. rats, dogs, monkeys or isolated organs, tissues and preparations thereof. Said compounds can be applied in vitro in the form of solutions, e.g. preferably aqueous solutions, and in vivo either enterally or parenterally advantageously orally or intravenously, e.g. within gelatin capsules, as starch suspensions or in aqueous solutions. The dosage in vitro may range between about $10^{-5}$ molar and $10^{-9}$ molar concentrations. The dosage in vivo may range between about 0.001 and 25 mg/kg/day, preferably between about 0.0025 and 10 mg/kg/day depending on the compound and the route of administration.

Adenosine-2 (A-2) receptor binding properties, indicative of the adenosine-2 receptor agonist activity of the compounds of the invention can be determined in vitro by determining their ability to inhibit the specific binding of $^3$H-5'-N-ethylcarboxamidoadenosine ($^3$H-NECA), e.g. essentially as described by R. F. Bruns et al, Mol. Pharmacol. 29, 331 (1986), in striatal membrane preparations from corpus striatum of male Sprague-Dawley rats. The concentration of a particular compound required to displace the specific binding of 4 nM $^3$H-NECA is determined in the presence of 50 nM cyclopentyladenosine.

Adenosine-1 (A-1) receptor binding properties of the compounds of the invention indicative of adenosine-1-receptor agonist activity can be determined, e.g., essentially according to R. F. Bruns et al in Proc. Natl. Acad. Sci. U.S.A. 77:5547 (1980), by determining their ability to inhibit the specific binding of $^3$H-cyclohexyladenosine ($^3$H-CHA) in rat brain membrane preparations from male Sprague-Dawley rats. The concentration of a particular compound required to displace the specific binding of 1 nm $^3$H-CHA is determined.

Selectivity for the adenosine-2 (A-2) receptor can be ascertained by comparing the relative potency in the two adenosine receptor assays.

Selective as adenosine-2 receptor agonists are e.g. compounds of formula II and III as defined above.

Indicative of in vivo adenosine receptor agonist activity, the hypotensive activity of the compounds of the invention can be measured in normotensive or spontaneous hypertensive rats on intravenous or oral administration.

Typically, the blood pressure lowering effect in normotensive rats can be determined as follows:

Adult male rats weighing 300–400 g are anesthetized using Inactin (100 mg/kg, i.p.). A femoral artery and contralateral vein are cannulated for direct blood pressure measurement and i.v. drug administration, respectively. Animals are allowed a 15 minute equilibration period before testing. Vehicle (1 ml/kg, i.v.) is administered over a 30 second period followed by a 0.3 ml saline flush administered over a 30 second period. Changes in diastolic blood pressure are recorded using a Beckman polygraph while heart rate is recorded as a derivative of the blood pressure pulse. The test compound is administered in the same manner as vehicle and a dose response curve is established. Percent changes in heart rate and blood pressure are recorded.

The blood pressure lowering effect in the spontaneous hypertensive rat is determined on oral administration as known in the art.

Antithrombotic activity can be demonstrated by measuring the inhibition of collagen-induced platelet aggregation.

Illustrative of the invention, the compound of Example 1 has an $IC_{50}$ of about $1 \times 10^{-7}$M in the in vitro adenosine-2 receptor binding assay, and effectively lowers blood pressure at a dose of about 10 mg/Kg p.o. in the spontaneous hypertensive rat model. Said compound of Example 1 also demonstrates in vitro activity in the adenosine-1 receptor binding assay indicative of more than 100 fold greater potency at the A-2 receptor than at the A-1 receptor. Further illustrative of the invention, the compound of Example 15(1) has an $IC_{50}$ of about $7 \times 10^{-8}$M in the in vitro adenosine-2 receptor binding assay.

The compounds of the invention can be prepared using a process comprising:

(a) reacting a compound of the formula

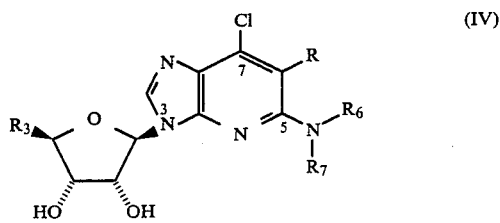

wherein $R_6$ represents $R_1$ as defined hereinabove except for aryl, $R_7$ represents hydrogen, lower alkyl or —COOR$_8$ in which $R_8$ represents lower alkyl, and R and $R_3$ have meaning as defined hereinabove, with hydrazine, and then deaminating the resulting 7-hydrazino derivative wherein $R_1$, $R_6$ and $R_3$ have meaning as defined for formula IV, and $R_7$ represents hydrogen or lower alkyl, to a corresponding compound of formula I; or (b) cyclizing a compound of the formula V, preferably wherein hydroxy groups are in protected form

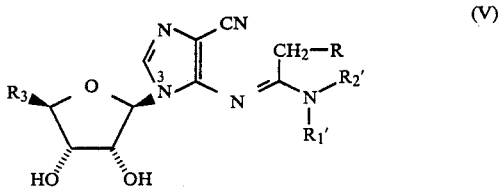

wherein R has meaning as defined hereinabove, and wherein $R_1'$ has meaning as defined hereinabove for $R_1$ provided that $R_1'$ does not represent hydrogen; and $R_1'$ may also represent benzyl optionally substituted by lower alkoxy; $R_2'$ represents lower alkyl or benzyl optionally substituted by lower alkoxy, to a compound of formula VI

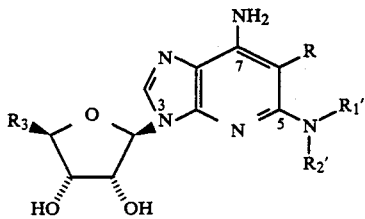

(VI)

wherein hydroxy groups are in protected form, and if $R_1'$ and/or $R_2'$ represent benzyl optionally substituted by lower alkoxy, debenzylating and deprotecting a said compound of formula VI, to the corresponding compound of formula I; or (c) condensing a compound of the formula VII

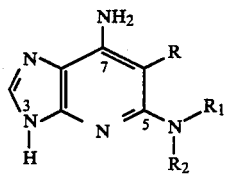

(VII)

wherein R, $R_1$ and $R_2$ have meaning as defined hereinabove with a compound of the formula VIII

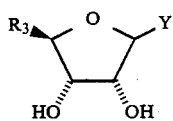

(VIII)

wherein $R_3$ has meaning as defined hereinabove, the hydroxy groups being in protected form, and Y represents a leaving group; and in any of the above processes, temporarily protecting any interfering reactive group(s) in the starting material and then subsequently removing any protecting groups in the resulting product, if so required, and, if desired, converting a resulting product into another compound of the invention, or converting a resulting compound into a salt thereof, or liberating a free compound from such a salt, and if appropriate isolating a substantially pure isomer from any resulting mixture of stereo isomeric forms.

The reactions leading to final products and intermediates are advantageously carried out in the absence of oxygen.

The preparation according to process (a) is carried out by first reacting a compound of formula IV with hydrazine, advantageously hydrazine monohydrate, at elevated temperature. In the case of a starting material of formula IV wherein $R_7$ represents —$COOR_8$, a corresponding hydrazine derivative wherein $R_7$ represents hydrogen is obtained. deamination of the resulting hydrazine is advantageously carried out using Raney nickel, e.g. in the presence of ammonia in an inert solvent such as methanol at elevated temperature. The hydrazine condensation and Raney nickel deamination are advantageously carried out in a sealed vessel.

The preparation according to process (a) is most advantageously used for the preparation of compounds of formula I wherein $R_3$ represents hydroxymethyl.

The starting materials can be prepared as exemplified below for compounds wherein $R_3$ represents hydroxymethyl.

A carbamate ester derivative of 7-chloro-5-amino-3H-imidazo[4,5-b]pyridine of formula XIII below wherein R and $R_6$ represent hydrogen and $R_8$ represents lower alkyl, e.g. ethyl N-(7-chloro-3H-imidazo[4,5-b]-pyridin-5-yl)-carbamate, is condensed, e.g. as the trimethylsilyl derivative, with the appropriate reactive ribose derivative, e.g. 1-O-acetyl-2,3,5-triacyl 1-β-D-ribofuranose, to form after removal of hydroxy protecting groups a compound of formula IVa

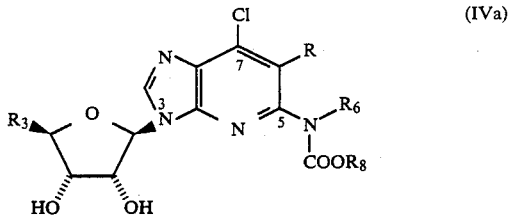

(IVa)

wherein R and $R_6$ represent hydrogen, $R_3$ represents hydroxymethyl and $R_8$ represents lower alkyl.

The N-(7-chloro-3H-imidazo[4,5-b]pyridin-5-yl)-carbamate ester starting material can be prepared e.g. as described in Rec. Trav. Chim. 93, 160 (1974).

Compounds of formula IVa can be prepared as reported in J. Heterocyclic Chemistry 15, 839 (1978) or as described herein.

In a resulting compound of formula IVa in which $R_6$ represents hydrogen, the vicinal hydroxy groups are protected preferably in the form of a ketal, e.g. as the isopropylidene, cyclohexylidene or benzylidene derivative, and with $R_3$ representing hydroxymethyl the primary hydroxy group is protected e.g. as the tetrahydropyranyl ether. Condensation with a compound of formula IX $$R_6'—X \qquad (IX)$$

wherein $R_6'$ represents $R_1$ as defined for the compounds of the invention except for hydrogen or aryl, and X represents a leaving group, particularly reactive esterified hydroxy, in the presence of a strong base in anhydrous medium, such as sodium hydride in dimethylformamide, and removal of ribose protecting groups with dilute acid yields a corresponding compound of formula IVa in which $R_6$ is now equivalent to $R_6'$.

A leaving group X in formula IX in the above processes represents reactive esterified hydroxy, especially halo, for example chloro, bromo or iodo, aliphatically or aromatically sustituted sulfonyloxy, for example methylsulfonyloxy or 4-methylphenylsulfonyloxy (tosyloxy).

In the above reaction sequence, $R_6'$—X may also represent e.g. an appropriately substituted allyl halide, and the double bond in the resulting protected product can be reduced by hydrogenation after the alkylation step.

The starting materials of formula IX are known in the art or are prepared by methods known in the art, e.g. as exemplified herein.

A starting material of formula IV, wherein $R_7$ represents lower alkyl, is prepared by treating an intermediate of formula IVa, wherein $R_6$ is equivalent to $R_6'$ as obtained above and wherein hydroxy groups are still in protected form, with e.g. aqueous sodium hydroxide to remove the —$COOR_8$ group, alkylating the resulting secondary amine with e.g. an alkyl halide in the presence of a base, e.g. sodium hydride, and then if desired removing the hydroxy protecting groups, e.g. with dilute hydrochloric acid.

The cyclization according to process (b) is carried out with a strong base, such as sodium hydride, in an inert anhydrous solvent such as dioxane. The vicinal secondary hydroxy groups in starting material of formula V are preferably protected in form of a ketal, e.g. as an isopropylidene, benzylidene or cyclohexylidene derivative and the primary hydroxy group (when $R_3$ is hydroxymethyl) may be protected e.g. as the tetrahydropyranyl ether, or the hydroxyl groups may also be protected as ester derivatives.

N-Debenzylation of group $R_1'$ and/or $R_2'$ representing optionally substituted benzyl is carried out as known in the art, e.g. using catalytic hydrogenation.

Process (b) can be used for the preparation of the compounds of formula I including those wherein $R_1$ represents aryl.

The starting materials of formula V in protected form can be prepared by condensing a compound of the formula X

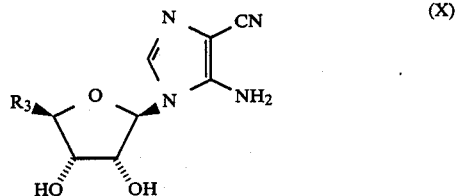

wherein $R_3$ has meaning as previously defined and hydroxy groups are protected in the form of ester or ether derivatives, with an acetamide derivative of the formula XI

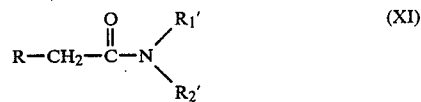

wherein $R_1'$ and $R_2'$ have meaning as defined for compounds of formula V in the presence of e.g. phosphoryl chloride or thionyl chloride in a polar solvent such as acetonitrile, or with a corresponding di-lower alkyl acetal derivative thereof of the formula XII

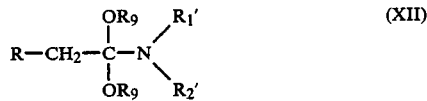

wherein $R_9$ represents lower alkyl, with or without an inert solvent such as acetonitrile.

The compounds of formula X, XI and XII are known or are prepared according to methods known in the art. Protected compounds of formula X are described e.g. in J. Chem. Soc. Perkin Trans. I., 1530 (1987) and Chemical Abstracts 71, 12561n (1969). The starting amides of formula XI are prepared from the corresponding amines and a reactive derivative of the appropriate carboxylic acid, e.g. of acetic acid, and can be converted to the corresponding acetals of formula XII, according to methods known in the art.

The condensation according to process (c) is carried out e.g. in the presence of a silylating reagent e.g. hexamethyldisilazane to first form in situ the trimethylsilyl derivative of a compound of formula VII which is then treated with a compound of formula VIII in protected form, such as 1,2,3,5-tetra-O-acetyl-β-D-ribofuranose, 2,3,5-tri-benzoyl-D-ribofuranosyl bromide, or 1-chloro-1-deoxy-N-ethyl-2,3,-O-(1-methylethylidene)-D-ribofuronamide, and the protecting groups are subsequently removed as required.

Leaving group Y in formula VIII represents preferably halogen, such as bromo or chloro, or lower alkanoyloxy, in particular acetoxy. Intermediates of formula VIII in protected form are known in the art.

The starting materials of formula VII can be prepared as follows:

For example, a carbamate ester derivative of 7-chloro-5-amino-3H-imidazo[4,5-b]pyridine of formula XIII

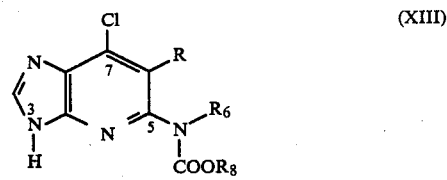

wherein R and $R_6$ represent hydrogen and $R_8$ represents lower alkyl, e.g. ethyl N-(7-chloro-3H-imidazo[4,5-b]pyridin-5-yl)-carbamate in which the imidazole ring nitrogen is protected, e.g. by benzyloxymethyl, is alkylated with a compound of formula IX, as defined hereinabove, to obtain, after treatment with dilute acid to remove the N-protecting group, a compound of the formula XIII wherein $R_6$ has meaning as defined herein for $R_1$ except for hydrogen or aryl. Such is converted to a compound of formula VII according to methodology in process (a), by condensation with hydrazine and treatment with Raney nickel.

Also 4-amino-5-cyanoimidazole may be condensed with a carboxylic acid amide, e.g. an acetamide derivative of the formula XI or XII under conditions as described under process (b) to obtain after debenzylation a compound of the formula VII. This method may be used for the preparation of intermediates of formula VII wherein $R_1$ represents aryl which can be converted to compounds of formula I wherein $R_1$ represents aryl.

In the preparation of esters and amides cited herein, reactive functional derivatives of the carboxylic acids are used and such represent, for example, anhydrides, acid halides, acid azides, lower alkyl esters and activated esters thereof. Mixed anhydrides are preferably such from pivalic acid, or a lower alkyl (ethyl, isobutyl) hemiester of carbonic acid; acid halides are for example chlorides or bromides; activated esters are for example succinimido, phthalimido or 4-nitrophenyl esters; lower alkyl esters are for example the methyl or ethyl esters.

In starting compounds and intermediates which are converted to the compounds of the invention in a manner described herein, functional groups present, such as amino and hydroxy, are optionally protected by conventional protecting groups that are common in preparative organic chemistry. Protected amino and hydroxy groups are those that can be converted under mild conditions into free amino and hydroxy groups without the molecular framework being destroyed or undesired side reactions taking place.

Well-known protecting groups that meet these conditions and their introduction and removal are described, for example, in J. F. W. McOmie, "Protective Groups in Organic Chemistry", Plenum Press, London, New York 1973, T. W. Greene, and "Protective Groups in Organic Synthesis", Wiley, New York 1984.

For example, a hydroxy group may be protected in the form of esters, e.g. as acyl derivatives such as the lower alkanoyl, benzoyl, benzyloxycarbonyl or lower alkoxycarbonyl derivative, or such hydroxy group may be protected in the form of ethers, e.g. as the lower alkyl, 2-tetrahydropyranyl, trityl or benzyl derivative.

Hydroxy groups on adjacent carbon atoms can also be protected e.g. in the form of ketals or acetals, such as lower alkylidene e.g. isopropylidene, benzylidene or 5- or 6-membered cycloalkylidene e.g. cyclopentylidene or cyclohexylidene derivatives.

In a resulting protected compound of formula I or intermediate, in which one or more of the functional groups are protected, the protected functional groups, e.g. hydroxy groups, can be liberated in a manner known per se, e.g. by means of solvolysis, especially hydrolysis with acid, or by hydrogenolysis.

The compounds of the invention or intermediates leading thereto can be converted into other compounds of the invention or corresponding intermediates using chemical methodology known in the art, and as illustrated herein.

For example, the conversion of compounds of formula I containing free hydroxy groups to ester derivatives thereof may be carried out by condensation with a corresponding carboxylic acid, advantageously as a reactive functional derivative thereof, according to acylation (esterification) procedures well-known in the art. For example, an appropriate carboxylic acid anhydride such as acetic anhydride is condensed with a compound of formula I in the presence of a suitable base, e.g. pyridine, triethylamine, 4-(dimethylamino)-pyridine, in an inert solvent such as acetonitrile.

Also, for example, halophenyl-, e.g. bromophenyl-substituted intermediates may be condensed with an olefin, e.g. with a lower alkyl ester of acrylic acid or with a styrene derivative, under conditions of the Heck reaction, and the resulting unsaturated products may then be hydrogenated to obtain the corresponding compounds having respectively an esterified carboxyethyl or phenethyl substituent on phenyl.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures preferably near the boiling point for the solvents used, and at atmospheric or superatmospheric pressure.

The invention further includes any variant of the present processes, in which an intermediate product obtainable at any stage thereof is used as starting material and the remaining steps are carried out, or in which the starting materials are formed under the reaction conditions, or in which the reaction components are used in the form of their salts or optically pure antipodes. Whenever desirable, the above processes are carried out after first suitably protecting any potentially interfering reactive functional groups, as illustrated herein.

Advantageously, those starting materials should be used in said reactions that lead to the formation of those compounds indicated above as being preferred.

The invention also relates to novel starting materials and processes for their manufacture.

Depending on the choice of starting materials and methods, the new compounds may be in the form of isomers, for example, as diastereomers, as optical isomers (antipodes), or as mixtures thereof.

In case diastereomeric mixtures of the above compounds or intermediates are obtained, these can be separated into the single racemic or optically active isomers by methods in themselves known, e.g. by fractional distillation, crystallization or chromatography.

Any racemic products or intermediates can be resolved into the optical antipodes, for example, by separation of diastereomeric salts formed from optically active acids or bases.

Basic racemic compounds can be resolved into the optical antipodes, for example, by separation of diastereomeric salts thereof, e.g., by the fractional crystallization of d- or l-(tartrate, dibenzoyltartrate, mandelate or camphorsulfonate) salts.

Acidic racemic compounds can likewise be resolved into optical antipodes by separation of diastereomeric salts thereof formed with an optically active base e.g. d- or l-alpha-methylbenzylamine, cinchonidine, cinchonine, quinine, quinidine, ephedrine, dehydroabietylamine, brucine or strychnine.

Finally, the compounds of the invention are either obtained in the free form, or as a salt thereof. For example, any resulting free base can be converted into a corresponding acid addition salt, preferably with the use of a pharmaceutically acceptable acid or anion exchange preparation, or resulting salts can be converted into the corresponding free bases, for example, with the use of a stronger base, such as a metal or ammonium hydroxide, or any basic salt, e.g., an alkali metal hydroxide or carbonate, or a cation exchange preparation. These or other salts, for example, the picrates, can also be used for purification of the bases obtained; the bases are then first converted into salts. In view of the close relationship between the free compounds and the compounds in the form of their salts, whenever a compound is referred to in this context, a corresponding salt is also intended, provided such is possible or appropriate under the circumstances.

The compounds, including their salts, may also be obtained in the form of their hydrates, or include other solvents used for the crystallization.

The present invention also relates to the use of the compounds of the invention for the preparation of pharmaceutical compositions, especially pharmaceutical compositions having adenosine-2 agonist activity which can be used for the treatment of e.g. cardiovascular conditions, such as hypertension, thrombosis and atherosclerosis.

The pharmaceutical compositions according to the invention are those suitable for enteral, such as oral or rectal, transdermal and parenteral administration to mammals, including man, for the treatment of diseases responsive to adenosine-2 agonist activity, such as hypertension, comprising an effective adenosine-2 stimulating amount of a compound of the invention, alone or in combination with one or more pharmaceutically acceptable carriers.

The pharmacologically active compounds of the invention are incorporated into pharmaceutical compositions comprising an effective amount thereof in conjunction or admixture with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid, its magnesium or calcium salts and/or polyethylene glycol; for tablets also (c) binders, e.g. magnesium aluminum silicate, starch paste, gelatin, tragacanth, methylcellulose, sodium carboxymethylcellulose and/or polyvinylpyrrolidone; if desired, (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

The present invention also relates to the use of compounds of the invention having adenosine-2 agonist properties and pharmaceutical compositions comprising said compounds for the treatment in mammals of disorders responsive to adenosine-2 agonist activity particularly cardiovascular conditions (e.g. hypertension and thrombosis).

One aspect relates advantageously to a method of enhancing adenosine-2 agonist activity in mammals and to the method of treating cardiovascular disorders in mammals, e.g. such responsive to adenosine-2 agonist activity, for example hypertension or thrombosis, using an effective amount of a compound of the invention, preferably in the form of the above-cited pharmaceutical compositions.

The dosage of active compound administered is dependent on the species of warm-blooded animal (mammal), the body weight, age and individual condition, and on the form of administration.

A unit dosage for a mammal of about 50 to 70 kg may contain between about 5 and 100 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between 15 and 100 mm Hg. The structure of final products, intermediates, and starting materials is confirmed by analytical methods, e.g. microanalysis and spectroscopic characteristics (e.g. MS, IR, NMR).

EXAMPLE 1

A suspension of 973 mg of ethyl N-(7-chloro-3-$\beta$-D-ribofuranosyl-3H-imidazo[4,5-b]pyridin-5-yl)-N-(2-cyclohexylethyl)-carbamate in 8 ml of hydrazine monohydrate is heated in a sealed tube at 120° for 24 hours. The solvent is evaporated in vacuo to afford ethyl N-[7-hydrazino-3-$\beta$-D-ribofuranosyl-N-(2-cyclohexylethyl)-3H-imidazo[4,5-b]pyridin-5-yl]-5-amine as a yellow foam. This foam is dissolved in 10 ml of methanol saturated with ammonia. To this solution is added 0.4 ml of a suspension of Raney nickel in methanol saturated with ammonia. This mixture is . heated in a sealed tube at 110° for 24 hours. The catalyst is filtered and washed with methanol. Evaporation of the solvents in vacuo gives a solid which is filtered through a plug of C-18 reverse phase silica gel using methanol as eluant. After removal of the methanol in vacuo, the remaining solid is recrystallized from methanol to give 7-amino-3-$\beta$-D-ribofuranosyl-N-(2-cyclohexylethyl)-3H-imidazo[4,5-b]pyridin-5-amine, m.p. 194°–195°, the compound of formula II wherein $R_1$ represents 2-cyclohexylethyl and $R_2$ represents hydrogen.

The starting material is prepared as follows:

To a mixture of 1.2 g ethyl N-(7-chloro-3H-imidazo[4,5-b]-pyridin-5-yl)-carbamate, prepared as described by Schelling and Salemink, Receuil 93 (6), 160 (1974), 2.52 g of 1-O-acetyl-2,3,5-tri-O-benzoyl-$\beta$-D-ribofuranose, 4.06 g potassium nonafluorobutanesulfonate and 0.56 g hexamethyldisilazane in 70 ml of acetonitrile is added 1.67 g of trimethylsilyl chloride. The mixture is heated to reflux under nitrogen for 21 hours. It is cooled, diluted with methylene chloride (100 ml) and treated with saturated aqueous sodium bicarbonate (50 ml). The organic phase is separated, and the aqueous layer is extracted with methylene chloride. The combined organic layers are washed with saturated aqueous sodium bicarbonate, then with brine, and then dried (sodium sulfate). Evaporation of the solvent in vacuo gives an oil which is dissolved in 100 ml of methanol saturated with ammonia, and the solution is stirred at room temperature for 40 hours. The clear solution is concentrated in vacuo, the residue is redissolved in water and washed twice with ether. The aqueous layer is concentrated in vacuo to give a glass. It is dissolved in hot acetonitrile, the solution is filtered, and the solvent is evaporated in vacuo to afford ethyl N-[7-chloro-3-$\beta$-D-ribofuranosyl-3H-imidazo[4,5-b]pyridin-5-yl]-carbamate, m.p 107°–111°.

A solution of 0.74 g of this triol, 3.85 g of 2,2-dimethoxypropane, and 0.13 g d-10-camphorsulfonic acid in 20 ml of acetone is stirred for 20 hours at room temperature under nitrogen. It is concentrated to dryness in vacuo, the residue is taken up in methylene chloride, and the solution is washed with saturated aqueous sodium bicarbonate. The aqueous phase is again extracted with methylene chloride and the combined extracts are washed with saturated aqueous sodium bicarbonate and water, and then dried (sodium sulfate). The solvent is evaporated in vacuo and the residue is recrystallized from acetonitrile to afford ethyl N-[7-chloro-3-[2,3-O-(1-methylethylidene)-$\beta$-D-ribofuranosyl]-3H-imidazo[4,5-b]pyridin-5-yl]carbamate, m.p. 138°–140°. A mixture of 7.4 g of this acetonide, 50 ml of 3,4-dihydro-2H-pyran, and 0.1 g of p-toluenesulfonic acid is stirred at room temperature for three hours. It is diluted with 100 ml methylene chloride, and washed with 50 ml saturated aqueous sodium bicarbonate. The aqueous layer is extracted with methylene chloride, and the combined organic layers are washed with saturated aqueous sodium bicarbonate, and dried (sodium sulfate). The solvents are evaporated in vacuo and the residual foam is purified by flash chromatography on silica gel using 9:1 methylene chloride/ethyl acetate, then ethyl acetate as eluants. In this way, ethyl N-[7-chloro-3-[2,3-O-(1-methylethylidene)-5-O-(2H-tetrahydropyran-2-yl)-β-D-ribofuranosyl]-3H-imidazo[4,5-b]pyridin-5-yl]-carbamate is isolated as a foam.

To a solution of 1.22 g of 2-cyclohexylethyl bromide and 1.56 g ethyl N-[7-chloro-3-[2,3-O-(1-methylethylidene)-5-O-(2H-tetrahydropyran-2-yl)-β-D-ribofuranosyl]-3H-imidazo[4,5-b]-pyridin-5-yl]-carbamate in 15 ml of dry dimethylformamide is added 0.25 g of sodium hydride (60% dispersion in mineral oil). After a few minutes the gas evolution subsides and the mixture is heated to 70° for 20 minutes. The reaction is quenched with water, and extracted three times with ethyl acetate. The organic extract is washed with water and dried (sodium sulfate). Evaporation of the solvent in vacuo gives an oil which is purified by flash chromatography on silica gel (40% ether/hexane followed by ether) to give ethyl N-[7-chloro-3-[2,3-O-(1-methylethylidene)-5-O-(2H-tetrahydropyran-2-yl)-β-D-ribofuranosyl]-3H-imidazo[4,5-b]pyridin-5-yl]-N-(2-cyclohexylethyl)-carbamate.

To a solution of 1.5 g of ethyl N-[7-chloro-3-[2,3-O-(1-methylethylidene)-5-O-(2H-tetrahydropyran-2-yl)-β-D-ribofuranosyl]-3H-imidazo[4,5-b]pyridin-5-yl]-N-(2-cyclohexyl-ethyl)-carbamate in 15 ml of methanol is added 15 ml of 1N HCl. This solution is heated to 55° for 8.5 hours. The reaction is neutralized with saturated aqueous sodium bicarbonate, and extracted three times with methylene chloride. The combined organic layers are dried (sodium sulfate) and the solvent is evaporated in vacuo to give ethyl N-[7-chloro-3-β-D-ribofuranosyl-3H-imidazo[4,5-b]pyridin-5-yl]-N-(2-cyclohexylethyl)-carbamate as a solid.

EXAMPLE 2

7-Amino-3-β-D-ribofuranosyl-N-(3-cyclohexylpropyl)-3H-imidazo[4,5-b]pyridin-5-amine, melting at 103°–109°, is prepared from 7-chloro-3-β-D-ribofuranosyl-N-(3-cyclohexylpropyl)-3H-imidazo[4,5-b]pyridin-5-amine essentially according to the procedures in Example 1, by treatment with hydrazine followed by Raney nickel.

The starting material is prepared as follows:

Ethyl N-[7-chloro-3-[2,3-O-(1-methylethylidene)-5-O-(2H-tetrahydropyran-2-yl)-β-D-ribofuranosyl]-3H-imidazo[4,5-b]pyridin-5-yl]-carbamate is alkylated with 3-cyclohexylpropyl 4-methylbenzenesulfonate (Becker, K. B., Boschung, A. F., Grob, C. A., Helv. Chim. Acta, 56, 2733 (1973)) essentially as described in Example 1 to give 7-chloro-3-[2,3-O-(1-methylethylidene)-5-O-(2H-tetrahydropyran-2-yl)-β-D-ribofuranosyl]-N-(3-cyclohexylpropyl)-3H-imidazo[4,5-b]pyridin-5-amine. Cleavage of carbamate ester occurs during alkylation step in this case.

The acetonide and the tetrahydropyranyl protecting groups are hydrolyzed essentially according to the procedures described in Example 1 to give 7-chloro-3-β-D-ribofuranosyl-N-(3-cyclohexylpropyl)-3H-imidazo[4,5-b]pyridin-5-amine.

EXAMPLE 3

7-Amino-3-η-D-ribofuranosyl-N-(4-cyclohexylbutyl)-3H-imidazo[4,5-b]pyridin-5-amine, melting at 88°–92°, is prepared from ethyl N-[7-chloro-3-[2,3-O-(1-methylethylidene)-5-O-(2H-tetrahydropyran-2-yl)-β-D-ribofuranosyl]-3H-imidazo-[4,5-b]pyridin-5-yl]-carbamate and 4-cyclohexylbutyl 4-methylbenzenesulfonate essentially according to the procedures in Examples 1 and 2.

The starting material is prepared as follows:

To a solution of 4-cyclohexanebutyric acid in 15 ml of THF at 0° is added 15 ml of a 1M solution of lithium aluminum hydride in THF. After the gas evolution ceases, the reaction is allowed to warm to room temperature. After stirring for six hours the reaction is cooled to 0° and quenched by carefully adding 2N HCl. The mixture is diluted with ether, and the layers are separated. The organic layer is then washed with saturated aqueous brine, and then dried (sodium sulfate/magnesium sulfate). Evaporation of the solvents in vacuo gives 4-cyclohexanebutanol as a clear oil. This oil is then dissolved in 20 ml of dry methylene chloride containing 3.5 ml of triethylamine and 2.85 g of p-toluenesulfonyl chloride. After stirring for 22 hours the reaction is quenched with water and stirred vigorously. The mixture is basified with 2N sodium hydroxide and extracted twice with methylene chloride. After drying (sodium sulfate), the solvents are evaporated in vacuo. Flash chromatography (50% methylene chloride/hexane) gives 4-cyclohexylbutyl 4-methylbenzenesulfonate as a clear oil.

EXAMPLE 4

7-Amino-3-β-D-ribofuranosyl-N-(cyclohexylmethyl)-3H-imidazo[4,5-b]pyridin-5-amine is prepared from ethyl N-[7-chloro-3-[2,3-O-(1-methylethylidene)-5-O-(2H-tetrahydropyran-2-yl)-β-D-ribofuranosyl]-3H-imidazo[4,5-b]pyridin-5-yl]-carbamate and bromomethylcyclohexane essentially according to the procedures in examples 1 and 2; NMR (CD$_3$OD): 7.98 (s, 1H), 5.81 (d, 1H), 5.68 (s, 1H), 4.84 (t, 1H), 4.31 (dd, 1H), 4.12 (dd, 1H), 3.89 (dd, 1H), 3.72 (dd, 1H), 3.02 (d, 2H).

EXAMPLE 5

7-Amino-3-β-D-ribofuranosyl-N-(2-(2-pyridinyl)-ethyl)-3H-imidazo[4,5-b]pyridin-5-amine is prepared from ethyl N-[7-chloro-3-[2,3-O-(1-methylethylidene)-5-O-(2H-tetrahydropyran-2-yl)-β-D-ribofuranosyl]-3H-imidazo[4,5-b]pyridin-5-yl]-carbamate and 2-(2-pyridinyl)-ethyl 4-methylbenzenesulfonate (Jones, G., Stanyer, J., J. Chem. Soc. C, 901 (1969)) essentially according to the procedures in examples 1 and 2; NMR(CD$_3$OD): 8.47 (d, 1H), 7.90 (s, 1H), 7.74 (dt, 1H), 7.35 (d, 1H), 7.23 (dt, 1H), 5.88 (d, 1H), 5.70 (s, 1H), 4.82 (t, 1H), 4.35 (dd, 1H), 4.11 (dd, 1H), 3.86 (dd, 1H), 3.71 (dd, 1H), 3.59 (dt, 2H), 3.07 (t, 2H).

EXAMPLE 6

7-Amino-3-β-D-ribofuranosyl-N-(2-phenylethyl)-3H-imidazo[4,5-b]pyridin-5-amine, melting at 198°–201°, is prepared from ethyl N-[7-chloro-3-[2,3-O-(1-methylethylidene)-5-O-(2H-tetrahydropyran-2-yl)-β-D-ribofuranosyl]-3H-imidazo[4,5-b]pyridin-5-yl]-carbamate and 2-phenylethyl iodide essentially according to the procedures outlined in Examples 1 and 2.

EXAMPLE 7

7-Amino-3-βD-ribofuranosyl-N-(3-phenylpropyl)-3H-imidazo-[4,5-b]pyridin-5-amine is prepared from ethyl [7-chloro-3-[2,3-O-(1-methylethylidene)-5-O-(2H-tetrahydropyran-2-yl)-β-D-ribofuranosyl]-3H-imidazo[4,5-b]pyridine-5-yl]-carbamate and 3-phenylpropyl bromide essentially according to the procedures outlined in Example 1 and 2; NMR (CD$_3$OD): 7.89 (s, 1H), 7.1–7.4 (m, 5H), 5.74 (d, 1H), 5.68 (s, 1H), 4.85 (t, 1H), 4.34 (dd, 1H), 4.16 (dd, 1H), 3.90 (dd, 1H), 3.75 (dd, 1H), 3.21 (t, 2H), 2.72 (t, 2H), 1.92 (quint, 2H).

EXAMPLE 8

7-Amino-3-β-D-ribofuranosyl-N-(2-methyl-2-phenylethyl)-3H-imidazo[4,5-b]pyridin-5-amine, melting at 147°–152°, is prepared from 7-chloro-3-β-D-ribofuranosyl-N-(2-methyl-2-phenylethyl)-3H-imidazo[4,5-b]pyridin-5-amine essentially according to the procedures outlined in Examples 1 and 2.

The starting material is prepared as follows:

Ethyl N-[7-chloro-3-[2,3-O-(1-methylethylidene)-5-O-(2H)-tetrahydropyran-2-yl)-β-D-ribofuranosyl]-3H-imidazo[4,5-b]pyridin-5-yl]-carbamate is alkylated with a mixture of 3-bromo-2-phenylpropene and 1-bromo-2-phenylpropene essentially as described in Examples 1 and 2 to give ethyl N-[7-chloro-3-[2,3-O-(1-methylethylidene)-5-O-(2H-tetrahydropyran-2-yl)-β-D-ribofuranosyl]-3H-imidazo[4,5-b]pyridin-5-yl]-N-(2-phenyl-2-propenyl)-carbamate.

A mixture of 230 mg of ethyl N-[7-chloro-3-[2,3-O-(1-methylethylidene)-5-O-(2H-tetrahydropyran-2-yl)-β-D-ribofuranosyl]-3H-imidazo[4,5-b]pyridin-5-yl]-N-(2-phenyl-2-propenyl)-carbamate and 59 mg of 5% rhodium on alumina in 10 ml of methanol is hydrogenated at room temperature with 1 atmosphere of hydrogen for 15 hours. The catalyst is filtered off and washed with methanol, and the solvents are evaporated to give ethyl N-[7-chloro-3-[2,3-O-(1-methylethylidene)-5-O-(2H-tetrahydropyran-2-yl)-β-D-ribofuranosyl]-3H-imidazo[4,5-b]pyridin-5-yl]-N-(2-methyl-(2-phenylethyl)-carbamate as a foam.

The acetonide and the tetrahydropyranyl ethers are hydrolyzed essentially according to the procedure described in Example 1 to give 7-chloro-3-β-D-ribofuranosyl-N-(2-methyl-2-phenylethyl)-3H-imidazo[4,5-b]pyridin-5-amine.

EXAMPLE 9

7 7-Amino-3-β-D-ribofuranosyl-N-methyl-N-(2-phenylethyl)-3H-imidazo[4,5-b]pyridin-5-amine is prepared from 7-chloro-3-β-D-ribofuranosyl-N-methyl-N-(2-phenylethyl)-3H-imidazo[4,5-b]pyridin-5-amine essentially according to the procedures in Examples 1 and 2; NMR (CD$_3$OD): 7.99 (s, 1H), 7.1–7.4 (m, 5H), 6.00 (d, 1H), 5.82 (s, 1H), 4.82 (t, 1H), 4.36 (t, 1H), 4.08 (dd, 1H), 3.6–3.9 (m, 5H), 2.92 (s, 3H), 2.89 (t, 2H).

The starting material is prepared as follows:

To a solution of 230 mg of ethyl N-[7-chloro-3-[2,3-O-(1-methylethylidene)-5-O-(2H-tetrahydropyran-2-yl)-⊖-D-ribofuranosyl]-3H-imidazo[4,5-b]pyridin-5-yl]-N-(2-phenylethyl)-carbamate (Example 6) in 5 ml of deoxygenated ethanol is added 2 ml of 5N aqueous (deoxygenated) sodium hydroxide. The reaction is heated to reflux under argon for one hour. The mixture is neutralized with saturated aqueous ammonium chloride and extracted three times with ethyl acetate. The combined organic layers are dried (sodium sulfate), and the solvents are evaporated in vacuo to give 7-chloro-3-[2,3-O-(1-methylethylidene)-5-O-(2H-tetrahydropyran-2-yl)-β-D-ribofuranosyl]-N-(2-phenylethyl)-3H-imidazo[4,5-b]pyridin-5-amine as an oil.

To a solution of 177 mg of 7-chloro-3-[2,3-O-(1-methylethylidene)-5-O-(2H-tetrahydropyran-2-yl)-β-D-ribofuranosyl]-N-(2-phenylethyl)-3H-imidazo[4,5-b]pyridin-5-amine in 4 ml of dry dimethylformamide is added 30 mg of sodium hydride (60% dispersion in mineral oil). The mixture is stirred for a few minutes, and then 0.060 ml of methyl iodide is added and the reaction is allowed to stir for four hours. The mixture is quenched with water and extracted three times with ethyl acetate. The organic extract is washed with water, and dried (sodium sulfate). Evaporation of the solvents in vacuo gives a red oil which is purified by flash chromatography on silica gel (25% ether/hexane, then ether) to give 7-chloro-3-[2,3-O-(1-methylethylidene)-5-O-(2H-tetrahydropyran-2-yl)-β-D-ribofuranosyl]-N-methyl-N-(2-phenylethyl)-3H-imidazo[4,5-b]pyridin-5-amine as a foam.

A solution of 150 mg of 7-chloro-3-[2,3-O-(1-methylethylidene)-5-O-(2H-tetrahydropyran-2-yl)-β-D-ribofuranosyl]-N-methyl-N-(2-phenylethyl)-3H-imidazo[4,5-b]pyridin-5-amine in 2.5 ml of methanol and 2.5 ml of 1 N HCl is stirred at 55° for 2 hours. The reaction is neutralized with saturated aqueous sodium bicarbonate, and extracted 3 times with ethyl acetate. The organic extract is dried (sodium sulfate), and the solvents are evaporated in vacuo to give an oil which is purified by flash chromatography on silica gel (2% ethanol/ethyl acetate followed by 5% ethanol/ethyl acetate followed by 10% ethanol/ethyl acetate) to give 2 7-chloro-3-β-D-ribofuranosyl-N-methyl-N-(2-phenylethyl)-3H-imidazo[4,5-b]pyridin-5-amine as a foam.

EXAMPLE 10

5-[1-(Dimethylamino)ethylideneamino]-1-[2,3-O-(1-methylethylidene)-β-D-ribofuranosyl]-imidazole-4-carbonitrile (0.45 g) is added to a suspension of sodium hydride (0.125 g) in dioxane (10 ml) and the mixture is heated under nitrogen at 110° over 1 hour. The mixture is poured into ice and extracted with ether. The ether extract is washed with water, then with saturated sodium chloride solution and dried over sodium sulfate and evaporated to dryness to yield solid product. Extraction of the aqueous layer with ethyl acetate gives a second crop of material. The combined solid is recrystallized from a small volume of ethyl acetate to afford pure 7-amino-3-[2,3-O-(1-methyl7 ethylidene)-β-D-ribofuranosyl]-N,N-dimethyl-3H-imidazo[4,5-b]pyridine-5-amine, m.p. 176°–178°.

The intermediate (450 mg) is stirred in a 9:1 mixture of trifluoroacetic acid and water (7 ml) at room temperature for one hour. The solution is concentrated to dryness at reduced pressure and the resulting material purified by chromatography on silica gel, with a 9:1 mixture of methylene chloride and ammonia-saturated methanol as eluant to afford 7-amino-3-β-D-ribofuranosyl-N,N-dimethyl-3H-imidazo[4,5-b]pyridine-5-amine; NMR (CD$_3$OD): 7.97 (s,1H), 5.95 (d,1H), 5.83 (s,1H), 4.9 (s,5H +H20), 4.85 (t,1H), 4.39 (t,1H), 4.08 (dd,1H), 3.6–3.9 (m,2H), 3.05 (s,6H).

The starting material is prepared as follows:

To a suspension of 0.56 g of 5-amino-1-[(2,3-O-(1-methylethylidene)-β-D-ribofuranosyl)]-1H-imidazole- 4-carbonitrile (Reese, Sangvi and Kuroda, J. C. S. Perkin Trans. I, 1987, 1530) in acetonitrile (10 ml) is added dimethylacetamide dimethylacetal (1.0 ml) and the mixture stirred under nitrogen at room temperature for 17 hours. It is concentrated under vacuum to remove residual solvent, the residue is redissolved in ether-acetonitrile, the solution is decolorized with charcoal, filtered and concentrated to dryness at reduced pressure. The residue is triturated with ether to produce the crystalline intermediate (m.p. 122°–5°) which may be purified by crystallization from ethyl acetate to give 5-[1-(dimethylamino)-ethylideneamino]-1-[2,3-O-(1-methylethylidene)-β-D-ribofuranosyl]-imidazole-4-carbonitrile, m.p. 127°–9°; I.R. (Nujol) 2209, 1609 cm$^{-1}$,

EXAMPLE 11

5-[1-(dimethylamino)-ethylideneamino]-1-(2,3,5-tri-O-acetyl-β-D-ribofuranosyl)-imidazole-4-carbonitrile is reacted with sodium hydride in dioxane as described in Example 10 and the crude product is reacted with methanolic ammonia at room temperature over 18 hours. The mixture is concentrated to dryness and purified by silica gel chromatography to afford 7-amino-3-β-D-ribofuranosyl-N,N-dimethyl-3H-imidazo[4,5-b]pyridine-5-amine.

The starting material is prepared as follows:

To a solution of 0.73 g of 5-amino-4-cyano-1-(2,3,5-tri-O-acetyl-β-D-ribofuranosyl)-imidazole, prepared as described by Suzuki and Kumashiro, Chem. Abstracts 71, 12561n (1969), and dimethylacetamide (0.70 g) in acetonitrile (5 ml) is added dropwise phosphoryl chloride (0.61 g) and the mixture is stirred under nitrogen for 20 hours at room temperature. The mixture is poured into 5% aqueous sodium carbonate and extracted with ethyl acetate and the organic layer washed with saturated sodium chloride solution and dried over sodium sulfate. The organic extract is concentrated to dryness at reduced pressure to afford 5-[1-(dimethylamino)-ethylideneamino]-1-(2,3,5-tri-O-acetyl-β-D-ribofuranosyl)-imidazole-4-carbonitrile as an oil.

EXAMPLE 12

Dimethylacetamide in Example 11 is replaced by an equimolar quantity of N-phenyl-N-benzylacetamide to yield 7-amino-3-β-D-ribofuranosyl-N-benzyl-N-phenyl-3H-imidazo[4,5-b]-pyridine-5-amine. Hydrogenolysis is ethanol containing acetic acid with 10% palladium on charcoal at 3 atmospheres pressure yields 7-amino-3-β-D-ribofuranosyl-N-phenyl-3H-imidazo[4,5-b]pyridine-5-amine.

EXAMPLE 13

Dimethylacetamide in Example 11 is replaced by an equimolar quantity of N-benzyl-N-(2-cyclohexylethyl)-acetamide to yield 7-amino-3-β-D-ribofuranosyl-N-(2-cyclohexylethyl)-N-benzyl-3H-imidazo[4,5-b]pyridine-5-amine. Hydrogenolysis as previously described in Example 12 yields 7-amino-3-β-D-ribofuranosyl-N-(2-cyclohexylethyl)-3H-imidazo[4,5-b]pyridine-5-amine, the compound obtained in Example 1.

EXAMPLE 14

(a) A mixture of 75 mg of 7-amino-N-(2-cyclohexylethyl)-3H-imidazo[4,5-b]pyridin-5-amine, 1 ml of hexamethyldisilazane, and 20 mg of ammonium sulfate is heated to reflux until the reaction becomes homogeneous. The solvent is evaporated in vacuo and to the residue is added 80 mg of 1-chloro-1-deoxy-N-ethyl-2,3-O-(1-methylethylidene)-D-ribofuronamide (R. R. Schmidt, G. R. Losch, and P. Fischer, Chem. Ber., 113, 2891 (1980)). The mixture is heated at 120° for 5 hours and then evaporated under vacuum. The residue is then purified by flash chromatography (5% methanol/methylene chloride) to give 1-[7-amino-5-[(2-cyclohexylethyl)amino]-3H-imidazo[4,5-b]pyridin-3-yl]-1-deoxy-N-ethyl-2,3-O-(1-methylethylidene)-β-D-ribofuronamide. To a mixture of 50 mg thereof in 1 ml of tetrahydrofuran is added 1 ml of 1N HCl. The reaction is stirred at room temperature for 2 hours, and the solvents are evaporated in vacuo. The residue is purified by flash chromatography on silica gel (10% methanol/methylene chloride) to give 1-[7-amino-5-[(2-cyclohexylethyl)-amino]-3H-imidazo[4,5-b]pyridin-3-yl]-1-deoxy-N-ethyl-β-D-ribofuronamide, the compound of formula III wherein $R_1$ represents 2-cyclohexylethyl, $R_4$ represents ethyl and $R_2$ represents hydrogen.

The starting material is prepared as follows:

To a solution of 124 mg of ethyl N-(7-chloro-3H-imidazo[4,5-b]pyridin-5-yl)-carbamate in 2 ml of dry dimethylformamide is added 50 mg of sodium hydride (60% dispersion in mineral oil). After stirring for 10 minutes, 0.11 ml of benzyl chloromethyl ether is added, and the reaction is stirred for 3 hours. The reaction is quenched with water and extracted 3 times with ethyl acetate. The organic extract is washed with water, and dried (sodium sulfate). Evaporation of the solvents in vacuo leaves a residue which is purified by flash chromatography on silica gel (ether) to give a mixture of ethyl N-[7-chloro-3-(benzyloxymethyl)-3H-imidazo[4,5-b]pyridin-5-yl]-carbamate and ethyl N-[7-chloro-1-(benzyloxymethyl)-1H-imidazo[4,5-b]pyridin-5-yl]carbamate. To a solution of 100 mg of this mixture in 2 ml of dry dimethylformamide is added 17 mg of sodium hydride (60% dispersion in mineral oil) and 210 mg of 2-cyclohexylethyl bromide. The mixture is heated at 70° for 5 hours, cooled to room temperature, and quenched with water. The mixture is extracted 3 times with ethyl acetate. The organic extract is washed with water, and dried (sodium sulfate). The solvents are evaporated in vacuo, and the residue is then dissolved in 2 ml of ethanol. To this solution is added 0.1 ml of concentrated HCl, and the reaction is heated to 70° for 5 hours. After cooling to room temperature, the reaction is neutralized with saturated aqueous sodium bicarbonate, and extracted 3 times with methylene chloride. The combined organic extracts are dried (sodium sulfate) and the solvents evaporated in vacuo to give a residue which is purified by flash chromatography on silica gel (5% methanol/methylene chloride) to give ethyl N-(7-chloro-3H-imidazo[4,5-b]pyridin-5-yl)-N-(2-cyclohexylethyl)-carbamate.

A mixture of 100 mg ethyl N-(7-chloro-3H-imidazo[4,5-b]pyridin-5-yl)-N-(2-cyclohexylethyl)-carbamate in 1 ml of hydrazine monohydrate is heated at 120° in a sealed tube for 24 hours. The solvent is evaporated in vacuo and 5 ml of methanol saturated with ammonia is added to the residue. This is followed by 0.1 ml of a suspension of Raney nickel in methanol saturated with ammonia. The mixture is heated in a sealed tube at 130° for 24 hours. The catalyst is filtered and washed with methanol, and the solvents are evaporated in vacuo to give a residue which is purified by flash chromatography (10% methanol saturated with ammonia/methylene chloride) to give 7-amino-N-(2-cyclohexylethyl)-3H-imidazo[4,5-b]pyridin-5-amine.

(b) Using 7-amino-N-phenyl-3H-imidazo[4,5-b]pyridin-5-amine as starting material, 1-(7-amino-5-anilino-3H-imidazo[4,5-b]pyridin-3-yl)-1-deoxy-N-ethyl-$\beta$-D-ribofuronamide is obtained.

The starting material can be prepared as follows:

5-Aminoimidazole-4-carbonitrile is condensed with N-benzyl-N-phenyl-acetamide in the presence of phosphoryl chloride in acetonitrile at room temperature to yield 5-[1-(N-phenyl-N-benzylamino)ethylideneamino]-imidazole-4-carbonitrile. Such is cyclized with sodium hydride in dioxane to yield 7-amino-N-phenyl-N-benzyl-3H-imidazo[4,5-b]pyridine-5-amine. Hydrogenolysis in ethanol with palladium on charcoal yields 7-amino-N-phenyl-3H-imidazo[4,5-b]pyridine-5-amine.

EXAMPLE 15

Prepared similarly to the methods described in the previous examples are the following compounds of the formula II wherein $R_2$ represents hydrogen and $R_1$ represents:

(a) hydrogen (e.g. by hydrogenolysis of a compound of formula II wherein $R_1$ and $R_2$ represent benzyl); hydrochloride salt, m.p. 105° dec., [alpha]$D^{25}$ = —67° (c, 1, H$_2$O);
(b) 2-(p-chlorophenyl)-ethyl;
(c) 2-cyclopentylethyl;
(d) 2-(p-ethoxycarbonylphenyl)-ethyl;
(e) 2-(tetrahydropyran-4-yl)-ethyl;
(f) 2-(1-adamantyl)-ethyl;
(g) 2-(2-norbornanyl)-ethyl;
(h) 2-(2-naphthyl)-ethyl;
(i) 2-(3-pyridyl)-ethyl;
(j) 2-(2-thienyl)-ethyl;
(k) 2-[p-(2-carboxyethyl)-phenyl]-ethyl;
(l) 2-(p-methoxyphenyl)-ethyl, m.p. 191°–193°
(m) 2-(p-trifluoromethylphenyl)-ethyl, m.p. 181°–184°
(n) 3-phenylpropyl;
(o) 2,2-diphenylethyl;
(p) 2-[p-(carboxymethoxy)-phenyl]-ethyl.
(q) 2-(p-fluorophenyl)-ethyl, m.p. 194°–195° (dec);
(r) 2-(o-methoxyphenyl)-ethyl, m.p. 163°–167°;
(s) 2-(p-methylphenyl)-ethyl, m.p. 187°–189°;
(t) 2-(m-methoxyphenyl)-ethyl, m.p. 162°–167°;
(u) 2-(m,p-dimethoxyphenyl)-ethyl, m.p. 188°–191°;

The amine starting material for compound (e), 2-(tetrahydropyran-4-yl)-ethylamine, can be prepared from tetrahydropyran-4-one e.g. by Wittig condensation with diethyl cyanomethyl phosphonate followed by hydrogenation and reduction with lithium aluminum hydride. The amine can be converted to a starting material of formula XI wherein $R_1'$ represents 2-(tetrahydropyran-4-yl)-ethyl and $R_2'$ represents benzyl.

The corresponding starting alcohol for compound (e) for conversion to a reactive halide or sulfonate ester of formula IX can in turn be prepared by condensation 4-tetrahydropyran-4-one with triethyl phosphonoacetate followed by hydrogenation of the double bond and subsequent reduction of the ester with lithium aluminum hydride.

The amine starting material for compound (k) is prepared as follows:

p-Bromophenylacetonitrile is first condensed with t-butyl acrylate under conditions of the palladium acetate catalyzed Heck reaction. The resulting acrylate is hydrogenated with palladium on charcoal catalyst followed by reduction (of the cyano group) with sodium borohydride in the presence of cobalt(II) chloride to yield t-butyl p-(2-aminoethyl)-phenylpropionate.

The corresponding starting material of formula IX is prepared as follows:

p-Bromophenylethanol is first condensed with t-butyl acrylate under conditions of the palladium acetate catalyzed Heck reaction. The resulting acrylate is hydrogenated with palladium on charcoal catalyst to yield t-butyl p-(2-hydroxyethyl)-phenylpropionate, which is converted to the corresponding tosylate by treatment with tosyl chloride in pyridine.

The starting amine for compound (p) is prepared by first condensing p-hydroxyphenylacetonitrile with t-butyl bromoacetate followed by reduction of the nitrile.

The starting material for the preparation of compound (u) according to example 1 is prepared as follows:

To a solution of 0.17g ethyl N-[7-chloro-3-[2,3-0-(1-methylethylidene)-5-0-(2H-tetrahydropyran-2-yl)-$\beta$-D-ribofuranosyl]-3H-imidazo-[4,5-b]pyridin-5-yl]-carbamate (see Example 1) in 2 ml of tetrahydrofuran is added 0.55 ml of a 1.96M solution of potassium hexamethyl-disilazane in tetrahydrofuran. The mixture is heated to 75° and stirred for 30 minutes. To this mixture is added 0.4 ml of dimethylformamide followed by 0.29g of 2-(3,4-dimethoxyphenyl)-ethyl 4-methylbenzenesulfonate. The reaction is heated for an additional 45 minutes. The reaction is quenched with water, diluted with saturated aqueous ammonium chloride, and extracted three times with ethyl acetate. The organic extract is washed with dilute aqueous ammonium chloride and dried (sodium sulfate). Evaporation of the solvent in vacuo gives an oil which is purified by flash chromatography on silica gel (methylene chloride followed by ether followed by 2% methanol/methylene chloride) to give ethyl N-[7-chloro-3-[2,3-0-(1-methylethylidene)-5-0-(2H-tetrahydropyran2-yl)-$\beta$-D-ribofuranosyl]-3H-imidazo[4,5-b]pyridin5-yl]-N-[2-(3,4-dimethoxyphenyl)-ethyl]-carbamate. Treatment with 1N hydrochloric acid yields ethyl-N-(7-ohloro-3-$\beta$-D-ribofuranosyl-3H-imidazo[4,5-b]pyridin-5yl)-N-[2-(3,4-dimethoxyphenyl)ethyl]-carbamate.

EXAMPLE 16

Prepared similarly to methods described in the previous examples are the compounds of formula III wherein $R_2$ represents hydrogen, $R_4$ represents ethyl and $R_1$ represents:

(a) 2-(p-chlorophenyl)-ethyl;
(b) 2-phenylethyl;
(c) 2-(1-adamantyl)-ethyl;
(d) 2-(2-norbornanyl)-ethyl;
(e) 2-(2-pyridyl)-ethyl;
(f) 2-(2-thienyl)-ethyl;
(g) 3-phenylpropyl;
(h) 2-cyclopentylethyl;
(i) 3-cyclohexylpropyl;
(j) 4-cyclohexylbutyl;
(k) 2-(p-trifluoromethylphenyl)-ethyl;
(l) 2-(p-methoxyphenyl)-ethyl;
(m) 2-[p-(2-carboxyethyl)-phenyl]-ethyl;
(n) hydrogen;
(o) 2,2-diphenylethyl;
(p) 2-[p-(carboxymethoxy)-phenyl]-ethyl;
(q) 2-(p-fluorophenyl)-ethyl;
(r) 2-(o-methoxyphenyl)-ethyl;
(s) 2-(p-methylphenyl)-ethyl;
(t) 2-(m-methoxyphenyl)-ethyl;
(u) 2-(m,p-dimethoxyphenyl)-ethyl.

EXAMPLE 17

A solution of 5-[1-(N-benzyl-N-phenylamino)ethylideneamino]-1-[2,3-0-(1-methylethylidene-β-D-ribofuranosyl]-imidazole-4-carbonitrile (1.8 g) in dry dioxane (15 ml) is added to a suspension of sodium hydride (60% in oil, 0.6 g, washed with hexane) in dioxane (15 ml) and heated under nitrogen at reflux for 1.5 hours. The mixture is poured into ice-water and extracted with ethyl acetate. The ethyl acetate layer is washed with water, then brine, dried over sodium sulphate and concentrated to dryness at reduced pressure to a foam. This is further purified using silica gel chromatography by elution first with 3:1, then with 1:1 methylene chloride—ethyl acetate to remove impurities, followed by isolation of the product by elution with ethyl acetate and evaporation of the solvent. The product (m.p. 93°-99°) is taken up in 95% ethanol (150 ml) and hydrogenated at 3 atmospheres pressure in the presence of palladium hydroxide (1.5 g) over 12 hours. The mixture is filtered and the filtrate concentrated to dryness at reduced pressure to afford crude product. Recrystallization from ethyl acetate gives the debenzylated acetonide, 7-amino-3-[2,3-O-(1-methylethylidene)-β-D-ribofuranosyl]-N-phenyl-3H-imidazo[4,5-b]pyridine-5-amine, m.p. 225°-228°. The acetonide (0.6 g) is added to an ice-cold solution of 90% trifluoroacetic acid (4 ml). After 1 hour, the solution is diluted with dry ether and the salt collected as a solid. It is taken up in bicarbonate solution and extracted with ethyl acetate. The ethyl acetate layer is washed with water, then brine, dried over sodium sulphate and concentrated to dryness. The residue is recrystallized from water to give 7-amino-3-β-D-ribofuranosyl-N-phenyl-3H-imidazo[4,5-b]pyridine-5-amine, the compound of example 12, m.p. 192°-195°, [alpha]D$^{25}$ = −19.3° (c=1.29 DMSO).

The starting material is prepared as follows:

To an ice-cold mixture of 5-amino-1-[2,3-0-(1-methylethylidene)-β-D-ribofuranosyl]-1H-imidazole-4-carbonitrile (40.2 g) in pyridine (145 ml) is added acetic anhydride (29ml) dropwise with stirring and moisture exclusion and the whole maintained at ambient temperature over 16 hours. It is recooled in an ice bath and treated dropwise with methanol (60 ml). After stirring 1 hour the mixture is concentrated to dryness at reduced pressure and the residue is taken up in methylene chloride, washed several times with water, dried over sodium sulphate and concentrated to an oil. This is triturated and stirred with ether to give the 5-0-acetyl-β-D-ribofuranosyl derivative as a solid. (m.p. 135°-137°).

A solution of 2.3 g of 5-amino-1-[2,3-0-(1-methylethylidene)-5-0-acetyl-β-D-ribofuranosyl]-1H-imidazole-4-carbonitrile in a mixture' of acetonitrile (25 ml) and N-benzylacetanilide (6.4 g) is treated dropwise under moisture exclusion with phosphoryl chloride (2.2 g) at room temperature overnight with stirring. The mixture is poured into ice-cold sodium bicarbonate solution and extracted with ethyl acetate. The organic layer is washed several times with sodium bicarbonate solution, then with water, then with brine and dried over sodium sulphate. The concentrated extract is purified by chromatography through silica gel using 5:1 methylene chloride, ethyl acetate followed by a 1 mixture of the same solvents. The product is stirred overnight in methanol saturated with ammonia (100 ml). The solution is concentrated to dryness at reduced pressure and the residue is taken up in ethyl acetate, the solution is washed with water, then brine, dried over sodium sulphate and concentrated to dryness. The material is further purified by chromatography with silica gel, using 1:1 methylene chloride and ethyl acetate followed by ethyl acetate alone to yield 5-[1-(N-benzyl-N-phenylamino)ethylideneamino]-1-[2,3-0-(1-methylethylidene)-β-D-ribofuranosyl]-imidazole-4-carbonitrile as a foam, m.p 68°-70°

EXAMPLE 18

A mixture of 7-amino-3-[2,3-O-(1-methylethylidene)-β-D-ribofuranosyl]-N-benzyl-N-(p-bromophenethyl)-3H-imidazo[4,5-b]pyridin-5-amine (1.78 g), benzyl acrylate (0.64 g), palladium acetate (7 mg), tri-o-tolylphosphine (36 mg) and triethylamine (1.97 g) under a nitrogen atmosphere is stirred at 140° over 18 hours. The mixture is treated with sodium bicarbonate solution and extracted with methylene chloride. The organic layer is dried over sodium sulphate, filtered and concentrated to dryness at reduced pressure. The residue is flash chromatographed through silica gel with 20:1 methylene chloride-methanol as eluent. Fractions containing the desired benzyl ester are combined and concentrated to dryness to a foam which crystallizes on treatment with methanol. It is dissolved in ethanol (100 mL), treated with palladium hydroxide on carbon (1.0 g) and hydrogenated at 3 atmospheres pressure and 60° over 8 hours. The warm mixture is filtered and the filtrate concentrated to dryness at reduced pressure. The residue is triturated with a minimal amount of methanol to afford 7-amino-3-[2,3-O-(1-methylethylidene)-.β-D-ribofuranosyl]-N-{2-[p-(2-carboxyethyl)-phenyl]-ethyl}-3H-imidazo[4,5-b]-pyridin- 5-amine, m.p. 215°-217°. The solid is stirred in 9:1 trifluoroacetic acid-water (2 mL) and after 1 hour the solution is treated with ether to yield the trifluoroacetate salt of 7-amino-3-β-D-ribofuranosyl-N-{2-[p-(2-carboxyethyl)-phenyl]-ethyl}-3H-imidazo-[4,5-b]-pyridin-5-amine. On treatment with HCl gas, a salt is precipitated. The salt is triturated with ether and collected to yield the dihydrochloride salt as a dihydrate, m.p. 111° dec.

The starting material is prepared as follows:

N-(p-bromophenethyl)-N-benzylacetamide is prepared by reacting a mixture of p-bromophenethylamine and benzaldehyde in 7:2 petroleum ether-acetic acid with borane-pyridine complex for two hours and the N-benzyl-p-bromophenethylamine obtained after workup is acetylated with acetyl chloride in methylene chloride in the presence of triethylamine overnight at room temperature. N-(p-bromophenethyl)-N-benzylacetamide is obtained pure after distillation, bp 216°-218° at 0.5 mm Hg.

N-(p-bromophenethyl)-N-benzylacetamide is condensed with 5-amino-1-[2,3-O-(1-methylethylidene)-β-D-ribofuranosyl]-1H-imidazole-4-carbonitrile as described in previous example to obtain 5-[1-(N-benzyl-N-p-bromophenethylamino)-ethylideneamino]-1-[2,3-O-(1-methylethylidene)-β-D-ribofuranosyl]imidazole-4-carbonitrile which is in turn cyclized to 7-amino-3-[2,3-O-(1-methylethylidene)-β-D-ribofuranosyl]-N-benzyl-N-(p-bromophenethyl)-3H-imidazo[4,5-b]pyridin-5-amine.

EXAMPLE 19

Prepared similarly to procedures described in examples 17 and 18 are the following:

(a) 7-Amino-3-β-D-ribofuranosyl-N-[2-(p-methylphenylethyl]-3H-imidazo[4,5-b]pyridin-5-amine dihydrochloride (the dihydrochloride salt of compound of Example 15s), m.p. 156°-161°, alpha$_D^{25}$ = -18.6° (c=1, DMSO) is obtained when N-(p-methylphenethyl)-N-benzylacetamide is substituted for N-benzylacetanilide in the reaction scheme of example 17. The acetamide, b.p. 177°-179° (0.2 mm), is prepared starting with p-tolylethylamine as illustrated in Example 18.

(b) 7-Amino-3-β-D-ribofuranosyl-N-[2-(p-fluorophenyl)-ethyl]-3H-imidazo[4,5-b]pyridin-5-amine dihydrochloride (the dihydrochloride salt of compound of example 15q), m.p. 146°-148°, alpha$_D^{25}$ = -14.9° (c=1.11, DMSO) is obtained when N-(p-fluorophenethyl)-N-benzylacetamide is substituted for N-benzylacetanilide in the sequence in Example 17. The acetamide, b.p. 162°-163° (0.9 mm), is prepared starting with p-fluorophenethylamine as illustrated in Example 18.

(c) 7-(Amino-3-.β-D-ribofuranosyl-N-[2-(p-fluorophenyl)-ethyl]-6-methyl-3H-imidazo[4,5-b]pyridin-5-amine dihydrochloride (the dihydrochloride salt of the compound of formula I wherein R represents methyl, $R_1$ represents 2-(p-fluorophenyl)ethyl, $R_2$ represents hydrogen and $R_3$ represents hydroxymethyl), m.p. 157°-160°, alpha$_D^{25}$ = +7.2° (c=1, EtOH) is obtained when N-(p-fluorophenethyl)-N-benzylpropionamide is substituted for N-benzylacetanilide in the reaction sequence of Example 17.

The propionamide is prepared by first condensing p-fluorophenethylamine with benzaldehyde under reductive conditions illustrated in Example 18, and then acylating the resulting N-benzyl-p-fluorophenethylamine with propionyl chloride as also illustrated in Example 18.

EXAMPLE 20

To an ice-cold solution of 90% aqueous trifluoroacetic acid (10 mL) is added 7-amino-3-[2,3-O-(1-methylethylidene)-β-D-ribofuranosyl]-N-{2-[p-phenylethyl)-phenyl]-ethyl}-3H-imidazo[4,5-b]-pyridin-5-amine (1.6 g) and stirred 1 hour at 0°-5°. The solution is diluted with ether, the resulting solid is collected and dissolved in methanol (75 ml), filtered free of a little impurity and treated with 6.5 N HCl in methanol (0.5 ml). After standing 1 hour, 7-amino-3-β-D-ribofuranosyl-N-{2-[p-(2-phenylethyl)-phenyl]-ethyl}[-3H-imidazo[4,5-b]-pyridin-5-amine dihydrochloride is collected, m.p. 150°-156°, alpha$_D^{25}$ = -15.0°, (c=1, MeOH).

The starting material is prepared as follows:

N-(p-bromophenethyl)-N-benzylacetamide is treated with styrene, palladium acetate, tri-o-tolylphosphine and triethylamine under conditions of the Heck reaction as illustrated in Example 18, to yield N-(p-styrylphenethyl)-N-benzylacetanilide, m.p. 136°-138°. Such is substituted in the sequence of Example 17 to yield 7-amino-3-[2,3-O-(1-methylethylidene)-β-D-ribofuranosyl]-N-benzyl-N-[2-(p-styrylphenyl)-ethyl]-3H-imidazo[4,5-b]-pyridin-5-amine. A solution thereof (2.6 g), palladium hydroxide (5.2 g) in 95% ethanol (200 mL) containing 1N HCl (10 mL) is hydrogenated at room temperature at 3 atmospheres pressure over 6 hours. It is filtered free of catalyst and the solution treated with propylene oxide (10 mL) at room temperature over 30 minutes. The solution is concentrated to dryness at reduced pressure, and the residue is triturated with ether to yield 7-amino-3-[2,3-O-(1-methylethylidene)-β-D-ribofuranosyl-N-{2-[p-(2-phenylethyl)-phenyl]-ethyl}-3H-imidazo[4,5-b]-pyridin-5-amine.

EXAMPLE 21

(a) Preparation of 10,000 tablets each containing 20 mg of the active ingredient:

Formula

| | |
|---|---|
| 7-Amino-3-β-D-ribofuranosyl-N-(2-cyclohexylethyl)-3H-imidazo-[4,5-b]pyridine-5-amine | 200.00 g |
| Lactose | 2,400.00 g |
| Corn starch | 125.00 g |
| Polyethylene glycol 6,000 | 150.00 g |
| Magnesium stearate | 40.00 g |
| Purified water | q.s. |

Procedure

All the powders are passed through a screen with openings of 0.6 mm. Then the drug substance, lactose, magnesium stearate and half of the starch are mixed in a suitable mixer. The other half of the starch is suspended in 65 ml of water and the suspension added to the boiling solution of the polyethylene glycol in 260 ml of water. The paste formed is added to the powders, which are granulated, if necessary, with an additional amount of water. The granulate is dried overnight at 35°, broken on a screen with 1.2 mm openings and compressed into tablets, using concave punches uppers bisected.

(b) Preparation of 1,000 capsules each containing 20 mg of the active ingredient:

Formula

| | |
|---|---|
| 7-Amino-3-β-D-ribofuranosyl-N-(2-cyclohexylethyl)-3H-imidazo-[4,5-b]pyridin-5-amine | 20.0 g |
| Lactose | 197.0 g |
| Modified starch | 80.0 g |
| Magnesium stearate | 3.0 g |

Procedure

All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 300 mg of said mixtures each, using a capsule filling machine.

Similarly prepared are tablets and capsules using other compounds of the invention exemplified herein.

What is claimed is:

1. A compound of the formula

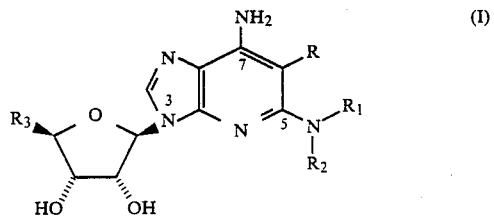

wherein R represents hydrogen, lower alkyl, carbocyclic aryl carbocyclic aryl-lower alkyl; $R_1$ represents hydrogen, lower alkyl, $C_3$-$C_7$-alkenyl, carbocyclic or heterocyclic aryl, carbocyclic or heterocyclic aryl-lower alkyl, C₃–C₇-cycloalkyl, or optionally lower alkyl substituted (C₃–C₇-cycloalkyl, bicycloheptyl, bicycloheptenyl, adamantyl, tetrahydropyranyl or tetrahydrothiopyranyl)-lower alkyl, or diaryl-lower alkyl; R₂ represents hydrogen or lower alkyl; R₃ represents hydroxymethyl or —CONHR₄ in which R₄ represents hydrogen, lower alkyl, aryl-lower alkyl, C₃–C₇-cycloalkyl, C₃–C₇-cycloalkyl-lower alkyl or hydroxy-lower alkyl; a pharmaceutically acceptable ester derivative, thereof in which one or more of the hydroxy groups are esterified in form of a pharmaceutically acceptable ester; or a pharmaceutically acceptable salt thereof.

2. A compound according to claim 1 of formula I wherein R represents hydrogen or lower alkyl; R₁ represents hydrogen, lower alkyl, C₃–C₇-cycloalkyl-lower alkyl, adamantyl-lower alkyl, bicycloheptyl-lower alkyl, aryl or aryl-lower alkyl in which aryl represents phenyl, thienyl, pyridyl, naphthyl, or phenyl substituted by one to three substituents selected from halogen, trifluoromethyl, lower alkoxy and lower alkyl, or aryl represents phenyl substituted by a substituent —W-Z in which W represents a direct bond, lower alkylene or oxy-lower alkylene, and Z represents hydroxy, cyano, carboxy, carboxy derivatized in the form of a pharmaceutically acceptable ester, carboxy derivatized in the form of a pharmaceutically acceptable amide, phenyl or phenyl substituted by halogen, trifluoromethyl, lower alkyl or lower alkoxy; or R₁ represents diaryl-lower alkyl in which aryl represents phenyl or phenyl substituted by halogen, trifluoromethyl, lower alkoxy or lower alkyl; R₂ represents hydrogen or lower. alkyl; R₃ represents hydroxymethyl or —CONHR₄ in which R₄ represents lower alkyl, hydroxy-lower alkyl, C₃–C₆-cycloralkyl, C₃–C₆-cycloalkyl-lower alkyl or aryl-lower alkyl in which aryl represents thienyl, naphthyl, phenyl, or phenyl substituted by halogen, trifluoromethyl, lower alkoxy, lower alkyl, hydroxy, cyano, carboxy, carboxy derivatized in the form of a pharmaceutically acceptable ester or carboxy derivatized in the form of a pharmaceutically acceptable amide; a pharmaceutically acceptable ester derivative thereof in which one or more of the hydroxy groups are esterified in the form of a pharmaceutically acceptable ester; or a pharmaceutically acceptable salt thereof.

3. A compound according to claim 2 of formula I wherein R₃ represents —CONHR₄; R, R₁, R₂ and R₄ have meaning as defined in said claim; a pharmaceutically acceptable ester derivative thereof as defined in said claim; or a pharmaceutically acceptable salt thereof.

4. A compound according to claim 2 of formula I wherein R₃ represents hydroxymethyl; R, R₁ and R₂ have meaning as defined in said claim; a pharmaceutically acceptable ester derivative thereof as defined in said claim; or a pharmaceutically acceptable salt thereof.

5. A compound according to claim 1 of the formula

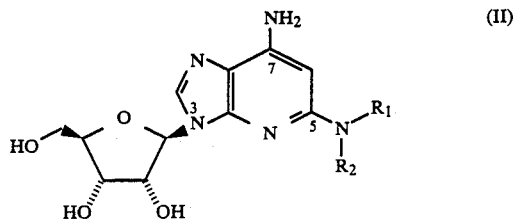

wherein R₁ represents bicycloheptyl-lower alkyl, adamantyl-lower alkyl, C₃—C₇-cycloalkyl-lower alkyl, aryl or aryl-lower alkyl in which aryl represents thienyl, pyridyl, phenyl or phenyl substituted by halogen, trifluoromethyl, lower alkoxy, lower alkyl or a substituent -W-Z in which W represents a direct bond, lower alkylene or oxy-lower alkylene, and Z represents hydroxy, cyano, carboxy, lower alkoxycarbonyl, carbamoyl, N-mono- or N,N-di-lower alkylcarbamoyl or phenyl; R₂ represents hydrogen or C₁–C₃-alkyl; a pharmaceutically acceptable prodrug ester derivative thereof in which one or more of the hydroxy groups are esterified in form of a pharmaceutically acceptable ester; or a pharmaceutically acceptable salt thereof.

6. A compound according to claim 5 of formula II wherein R₁ represents —(CH₂)n—R₅; n represents an integer from 2 to 5 inclusive; R₅ represents thienyl, pyridyl, phenyl or phenyl substituted by halogen, trifluoromethyl, lower alkoxy, lower alkyl or by a substituent —W-Z in which W represents a direct bond, C₁–C₄-alkylene or oxy-C₁–C₃-alkylene and Z represents hydroxy, cyano, carboxy, lower alkoxycarbonyl, carbamoyl, N-mono- or N,N-di-lower alkylcarbamoyl or phenyl; or R₅ represents C₅–C₇-cycloalkyl, norbornanyl or adamantyl; R₂ represents hydrogen; a pharmaceutically acceptable ester derivative thereof in which one or more of the hydroxy groups are esterified in form of a pharmaceutically acceptable ester; or a pharmaceutically acceptable salt thereof.

7. A compound according to claim 5 of formula II wherein R₁ represents thienyl, pyridyl, phenyl or phenyl substituted by halogen, trifluoromethyl, lower alkoxy, lower alkyl, hydroxy, cyano, carboxy, lower alkoxycarbonyl, carbamoyl, N-mono or N,N-di-lower alkylcarbamoyl; R₂ represents hydrogen; a pharmaceutically acceptable prodrug ester derivative thereof in which one or more of the hydroxy groups are esterified in form of a pharmaceutically acceptable ester; or a pharmaceutically acceptable salt thereof.

8. A compound according to claim 6 wherein R₅ represents cyclohexyl, phenyl or phenyl substituted by C₁–C₄-alkyl, C₁–C₄-alkoxy or trifluoromethyl.

9. A compound according to claim 1 of formula III

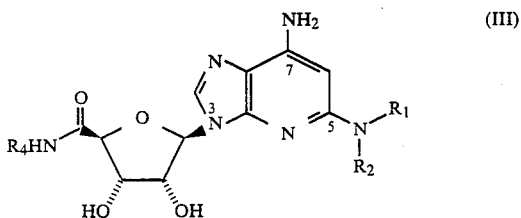

wherein R₁ represents bicycloheptyl-lower alkyl, adamantyl-lower alkyl, C₃–C₇-cycloalkyl-lower alkyl, aryl or aryl-lower alkyl in which aryl represents thienyl, pyridyl, phenyl or phenyl substituted by halogen, trifluoromethyl, lower alkoxy, lower alkyl or a substituent —W-Z in which W represents a direct bond, lower alkylene or oxy-lower alkylene, and Z represents hydroxy, cyano, carboxy, lower alkoxycarbonyl, carbamoyl, N-mono- or N,N-di-lower alkylcarbamoyl or phenyl; $R_2$ represents hydrogen; $R_4$ represents $C_1$-$C_4$-alkyl, cyclopropyl or hydroxy-$C_2$-$C_4$-alkyl; a pharmaceutically acceptable prodrug ester derivative thereof in which the hydroxy groups are esterified in form of a pharmaceutically acceptable ester; or a pharmaceutically acceptable salt thereof.

10. A compound according to claim 9 of formula III wherein $R_1$ represents —$(CH_2)_n$-$R_5$; n represents an integer from 2 to 5 inclusive; $R_5$ represents thienyl, pyridyl, phenyl or phenyl substituted by halogen, trifluoromethyl, lower alkoxy, lower alkyl or by a substituent —W-Z in which W represents a direct bond, $C_1$-$C_4$-alkylene or oxy-$C_1$-$C_3$-alkylene and Z represents hydroxy, cyano, carboxy, lower alkoxycarbonyl, carbamoyl, N-mono- or N,N-di-lower alkylcarbamoyl or phenyl; or $R_5$ represents $C_5$-$C_7$-cycloalkyl, norbornanyl or adamantyl; $R_2$ represents hydrogen; $R_4$ represents $C_1$-$C_3$-alkyl or cyclopropyl; a pharmaceutically acceptable prodrug ester derivative thereof in which the hydroxy groups are esterified in form of a pharmaceutically acceptable ester; or a pharmaceutically acceptable salt thereof.

11. A compound according to claim 10 wherein $R_5$ represents cyclohexyl, phenyl or phenyl substituted by $C_1$-$C_4$-alkyl, $C_1$-$C_4$-alkoxy or trifluoromethyl.

12. A compound according to claim 9 of formula III wherein $R_1$ represents thienyl, pyridyl, phenyl or phenyl substituted by halogen, trifluoromethyl, lower alkoxy, lower alkyl, hydroxy, cyano, carboxy, lower alkoxycarbonyl, carbamoyl, N-mono or N,N-di-lower alkylcarbamoyl; $R_2$ represents hydrogen; $R_4$ represents $C_1$-$C_3$-alkyl or cyclopropyl; a pharmaceutically acceptable prodrug ester derivative thereof in which the hydroxy groups are esterified in form of a pharmaceutically acceptable ester; or a pharmaceutically acceptable salt thereof.

13. A compound according to claim 8 being 7-amino-3-β-D-ribofuranosyl-N-(2-cyclohexylethyl)-3H-imidazo[4,5-b]-pyridin-5-amine, of formula II wherein $R_1$ represents 2-cyclohexylethyl and $R_2$ represents hydrogen, or a pharmaceutically acceptable salt thereof.

14. A compound according to claim 8 being 7-amino-3-β-D-ribofuranosyl-N-(3-cyclohexylpropyl)-3H-imidazo[4,5-b]-pyridin-5-amine, of formula II wherein $R_1$ represents 3-cyclohexylpropyl and $R_2$ represents hydrogen; or a pharmaceutically acceptable salt thereof.

15. A compound according to claim 8, being 7-amino-3-β-D-ribofuranosyl-N-(2-phenylethyl)-3H-imidazo[4,5-b]pyridin-5-amine, of formula II wherein $R_1$ represents 2-phenylethyl and $R_2$ represents hydrogen; or a pharmaceutically acceptable salt thereof.

16. A compound according to claim 6 wherein in —$(CH_2)_n$-$R_5$, n represents the integer 2, 3 or 4; and $R_5$ represents phenyl or phenyl substituted by $C_1$-$C_4$-alkyl, $C_1$-$C_4$-alkoxy, halogen or trifluoromethyl; or $R_5$ represents phenyl substituted by phenethyl.

17. A compound according to claim 6, being 7-amino-3-β-D-ribofuranosyl-N-[2-(p-fluorophenyl)ethyl]-3H-imidazo[4,5-b]pyridin-5-amine, of formula II wherein $R_1$ represents 2-(p-fluorophenyl)-ethyl and $R_2$ represents hydrogen; or a pharmaceutically acceptable salt thereof.

18. A compound according to claim 6, being 7-amino-3-β-D-ribofuranosyl-N-[2-(p-methoxyphenyl)ethyl]-3H-imidazo[4,5-b]pyridin-5-amine, of formula II wherein $R_1$ represents 2-(p-methoxyphenyl)ethyl and $R_2$ represents hydrogen; or a pharmaceutically acceptable salt thereof.

19. A compound according to claim 6, being 7-amino-3-β-D-ribofuranosyl-N-[2-(p-methylphenyl)ethyl]-3H-imidazo[4,5-b]pyridin-5-amine, of formula II wherein $R_1$ represents 2-(p-methylphenyl)ethyl and $R_2$ represents hydrogen; or a pharmaceutically acceptable salt thereof.

20. A pharmaceutical composition having adenosine-2 agonist activity suitable for administration to a mammal comprising an effective amount of a compound of claim 1 in combination with one or more pharmaceutically acceptable carriers.

21. A method of enhancing adenosine-2 agonist activity in mammals comprising the administration to a mammal in need thereof of an effective adenosine-2 agonist amount of a compound of claim 1 or of a pharmaceutical composition comprising a said compound.

22. A method of treating cardiovascular disorders in mammals which are responsive to adenosine-2-agonist activity comprising the administration to a mammal in need thereof of an effective adenosine-2-agonist amount of a compound of claim 1 or of a pharmaceutical composition comprising a said compound.

23. A method according to claim 22 of treating hypertension.

24. A method according to claim 22 of treating thrombosis.

* * * * *